US010233211B2

(12) United States Patent
Moya et al.

(10) Patent No.: US 10,233,211 B2
(45) Date of Patent: *Mar. 19, 2019

(54) PURIFICATION OF PROTEINS

(71) Applicant: EMD Millipore Corporation, Billerica, MA (US)

(72) Inventors: Wilson Moya, Concord, MA (US); Jad Jaber, Nashua, NH (US)

(73) Assignee: EMD Millipore Corporation, Burlington, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/955,024

(22) Filed: Jul. 31, 2013

(65) Prior Publication Data

US 2013/0317204 A1    Nov. 28, 2013

Related U.S. Application Data

(60) Division of application No. 12/316,708, filed on Dec. 16, 2008, now Pat. No. 8,569,464, which is a continuation-in-part of application No. 12/004,319, filed on Dec. 20, 2007, now Pat. No. 8,362,217.

(60) Provisional application No. 60/876,330, filed on Dec. 21, 2006.

(51) Int. Cl.
C07K 1/32    (2006.01)
C07K 1/30    (2006.01)

(52) U.S. Cl.
CPC . *C07K 1/32* (2013.01); *C07K 1/30* (2013.01)

(58) Field of Classification Search
None
See application file for complete search history.

(56) References Cited

U.S. PATENT DOCUMENTS

| | | | |
|---|---|---|---|
| 2,923,669 A | 2/1960 | Poitras | |
| 3,211,645 A | 10/1965 | Ferrari | |
| 3,556,302 A | 1/1971 | Agranant | |
| 3,565,973 A | 2/1971 | Michaels | |
| 3,632,507 A | 1/1972 | Witt | |
| 3,702,806 A | 11/1972 | Oliva | |
| 3,737,377 A | 6/1973 | Sternberg | |
| 3,859,212 A | 1/1975 | Smalley et al. | |
| 3,968,037 A | 7/1976 | Morgan et al. | |
| 4,045,377 A | 8/1977 | Pearson | |
| 4,055,469 A | 10/1977 | Snoke et al. | |
| 4,200,695 A | 4/1980 | Chong et al. | |
| 4,215,198 A | 7/1980 | Gordon | |
| 4,305,829 A | 12/1981 | Kelsey et al. | |
| 4,317,726 A | 3/1982 | Shepel | |
| 4,359,537 A | 11/1982 | Chong | |
| 4,371,674 A | 2/1983 | Hertel et al. | |
| 4,380,590 A | 4/1983 | Chong | |
| 4,382,028 A | 5/1983 | Paget | |
| 4,450,078 A | 5/1984 | Walker et al. | |
| 4,515,893 A | 5/1985 | Kung et al. | |
| 4,528,933 A | 7/1985 | Allen | |
| 4,536,294 A | 8/1985 | Guillet et al. | |
| 4,676,980 A | 6/1987 | Segal et al. | |
| 4,780,409 A | 10/1988 | Monji et al. | |
| 4,816,567 A | 3/1989 | Cabilly et al. | |
| 4,828,701 A | 5/1989 | Cussler | |
| 4,839,046 A | 6/1989 | Chandler | |
| 4,863,613 A | 9/1989 | Johnson et al. | |
| 4,904,385 A | 2/1990 | Wessling et al. | |
| 4,912,032 A | 3/1990 | Hoffman et al. | |
| 4,925,785 A | 5/1990 | Wang et al. | |
| 4,968,435 A | 11/1990 | Neff et al. | |
| 5,003,047 A | 3/1991 | Yarmush et al. | |
| 5,047,511 A | 9/1991 | Mehrotra | |
| 5,091,178 A | 2/1992 | Hellstrom et al. | |
| 5,091,313 A | 2/1992 | Chang | |
| 5,116,754 A | 5/1992 | Fraser et al. | |
| 5,139,031 A | 8/1992 | Guirguis | |

(Continued)

FOREIGN PATENT DOCUMENTS

CN    1483805 A    3/2004
CN    101096699 A    1/2008
(Continued)

OTHER PUBLICATIONS

Hilbrig et al. "Protein purification by affinity precipitation" J. Chromatography B, 790 (2003) 79-90.*
Journal of Molecular Biology, vol. 227, No. 2, Sep. 1992, pp. 381-388, "By-passing Immunisation: Human Antibodies from Synthetic Repertoires of Germline VH Gene Segments Rearranged in vitro", Hoogenboom, et al.
Molecular Immunology, vol. 28, No. 9, Sep. 1991, pp. 1027-1037, "Construction and expression of antibody-tumor necrosis factor fusion proteins", Hoogenboom, et al.

(Continued)

*Primary Examiner* — Daniel E Kolker
*Assistant Examiner* — James L Rogers
(74) *Attorney, Agent, or Firm* — Nields, Lemack & Frame, LLC

(57) ABSTRACT

The present invention relates to a selectively soluble polymer capable of binding to a desired molecules in an unclarified mixture containing various biological materials and the methods of using such a polymer to purify a molecule from such a mixture. The polymer is soluble in the mixture under a certain set of process conditions such as pH or temperature and/or salt concentration and is rendered insoluble and precipitates out of solution upon a change in the process conditions. The polymer is capable of binding to the desired molecule (protein, polypeptide, etc) and remains capable of binding to that molecule even after the polymer is precipitated out of solution. The precipitate can then be filtered out from the remainder of the stream and the desired biomolecule is recovered such as by elution and further processed.

3 Claims, 3 Drawing Sheets

(56) References Cited

U.S. PATENT DOCUMENTS

| | | | |
|---|---|---|---|
| 5,152,903 A | 10/1992 | Neff et al. |
| 5,164,057 A | 11/1992 | Mori et al. |
| 5,171,450 A | 12/1992 | Hoots |
| 5,208,161 A | 5/1993 | Saunders et al. |
| 5,238,545 A | 8/1993 | Yoshioka et al. |
| 5,258,122 A | 11/1993 | Ha et al. |
| 5,324,787 A | 6/1994 | Pinschmidt, Jr. et al. |
| 5,340,865 A | 8/1994 | Neff et al. |
| 5,342,581 A | 8/1994 | Sanadi |
| 5,354,481 A | 10/1994 | Neff et al. |
| 5,354,801 A | 10/1994 | O'Toole |
| 5,374,971 A | 12/1994 | Clapp et al. |
| 5,430,110 A | 7/1995 | Ahlers et al. |
| 5,512,480 A | 4/1996 | Sandstrom et al. |
| 5,525,519 A | 6/1996 | Woiszwillo |
| 5,573,675 A | 11/1996 | Sommese et al. |
| 5,599,719 A | 2/1997 | Woiszwillo et al. |
| 5,622,700 A | 4/1997 | Jardieu et al. |
| 5,622,857 A | 4/1997 | Goffe |
| 5,672,347 A | 9/1997 | Aggarwal et al. |
| 5,684,107 A | 11/1997 | Schneider et al. |
| 5,693,762 A | 12/1997 | Queen et al. |
| 5,714,338 A | 2/1998 | Wai Fei et al. |
| 5,721,108 A | 2/1998 | Robinson et al. |
| 5,725,856 A | 3/1998 | Hudziak et al. |
| 5,728,559 A | 3/1998 | Nilsson et al. |
| 5,733,507 A | 3/1998 | Zakim |
| 5,736,137 A | 4/1998 | Anderson et al. |
| 5,739,383 A | 4/1998 | Yoon et al. |
| 5,770,358 A | 6/1998 | Dower et al. |
| 5,807,489 A | 9/1998 | Farinato et al. |
| 5,840,804 A | 11/1998 | Carl et al. |
| 5,840,851 A | 11/1998 | Plomer et al. |
| 5,846,816 A | 12/1998 | Forth |
| 5,879,564 A | 3/1999 | Farinato |
| 5,929,214 A | 7/1999 | Peters et al. |
| 5,939,485 A * | 8/1999 | Bromberg .............. A41C 3/10 524/556 |
| 5,962,649 A | 10/1999 | Noda et al. |
| 5,994,560 A | 11/1999 | Yoon et al. |
| 5,998,588 A | 12/1999 | Hoffman et al. |
| 6,024,955 A | 2/2000 | Asano et al. |
| 6,121,428 A | 9/2000 | Blank et al. |
| 6,127,526 A | 10/2000 | Blank |
| 6,133,047 A | 10/2000 | Elaissari et al. |
| 6,139,746 A | 10/2000 | Kopf |
| 6,147,176 A | 11/2000 | Neff et al. |
| 6,153,104 A | 11/2000 | Robertson |
| 6,191,242 B1 | 2/2001 | Ryles et al. |
| 6,197,522 B1 | 3/2001 | Keller et al. |
| 6,221,655 B1 | 4/2001 | Fung et al. |
| 6,245,555 B1 | 6/2001 | Curtis |
| 6,258,275 B1 | 7/2001 | Freitag et al. |
| 6,294,622 B1 | 9/2001 | Barajas et al. |
| 6,300,142 B1 | 10/2001 | Andrewes et al. |
| 6,307,013 B1 | 10/2001 | Chivers |
| 6,358,730 B1 | 3/2002 | Kane |
| 6,367,749 B2 | 4/2002 | Valiulis |
| 6,372,141 B1 | 4/2002 | Okano et al. |
| 6,374,684 B1 | 4/2002 | Dority |
| 6,420,487 B1 | 7/2002 | Vaidya et al. |
| 6,454,950 B1 | 9/2002 | Tjerneld et al. |
| 6,521,341 B1 | 2/2003 | Elaissari et al. |
| 6,534,633 B1 | 3/2003 | Weidanz et al. |
| 6,538,089 B1 | 3/2003 | Samra et al. |
| 6,544,424 B1 | 4/2003 | Shevitz |
| 6,565,872 B2 | 5/2003 | Wu et al. |
| 6,582,926 B1 | 6/2003 | Chilkoti |
| 6,605,714 B2 | 8/2003 | Vaidya et al. |
| 6,638,918 B2 | 10/2003 | Davison et al. |
| 6,641,735 B1 | 11/2003 | Yoshizako et al. |
| 6,673,598 B1 | 1/2004 | Akers et al. |
| 6,676,840 B2 | 1/2004 | Tarbet et al. |
| 6,689,836 B2 | 2/2004 | Vaidya et al. |
| 6,706,187 B1 | 3/2004 | Okano et al. |
| 6,709,862 B2 | 3/2004 | Curtis |
| 6,716,593 B1 | 4/2004 | Robins et al. |
| 6,737,235 B1 | 5/2004 | Cros et al. |
| 6,765,081 B2 | 7/2004 | Lin et al. |
| 6,770,758 B2 | 8/2004 | Pan et al. |
| 6,805,793 B2 | 10/2004 | Yoshizako et al. |
| 6,821,515 B1 | 11/2004 | Cleland et al. |
| 6,830,670 B1 | 12/2004 | Viovy et al. |
| 6,852,819 B2 | 2/2005 | Ohnishi et al. |
| 6,858,694 B2 | 2/2005 | Ohnishi et al. |
| 6,863,437 B2 | 3/2005 | Ohnishi et al. |
| 6,867,268 B2 | 3/2005 | Vaidya et al. |
| 6,926,832 B2 | 8/2005 | Collins et al. |
| 6,956,077 B1 | 10/2005 | Akiyama et al. |
| 6,967,085 B1 | 11/2005 | Hughes et al. |
| 6,974,660 B2 | 12/2005 | Manias et al. |
| 7,001,953 B2 | 2/2006 | Chen et al. |
| 7,011,930 B2 | 3/2006 | Manias et al. |
| 7,012,136 B2 | 3/2006 | Yamanaka et al. |
| 7,052,917 B1 | 5/2006 | Ohnishi et al. |
| 7,070,696 B2 | 7/2006 | Weir et al. |
| 7,083,948 B1 | 8/2006 | Sassenfeld et al. |
| 7,157,603 B2 | 1/2007 | Hilbrig |
| 7,160,971 B2 | 1/2007 | Mallapragada et al. |
| 7,169,908 B2 | 1/2007 | Lester et al. |
| 7,195,925 B2 | 3/2007 | Ohnishi et al. |
| 7,300,545 B2 | 11/2007 | Ohara et al. |
| 7,355,020 B2 | 4/2008 | Yamanaka et al. |
| 7,364,859 B2 | 4/2008 | Chilkoti |
| 7,377,686 B2 | 5/2008 | Hubbard |
| 7,393,698 B2 | 7/2008 | Furukawa et al. |
| 7,422,724 B1 | 9/2008 | Manginell et al. |
| 7,429,458 B2 | 9/2008 | Chilkoti |
| 7,442,515 B2 | 10/2008 | Ratner et al. |
| 7,514,007 B2 | 4/2009 | Chen et al. |
| 7,541,167 B2 | 6/2009 | Dave et al. |
| 7,547,747 B2 | 6/2009 | Hashimoto et al. |
| 7,553,658 B2 | 6/2009 | Kepka et al. |
| 7,556,835 B2 | 7/2009 | Hultin et al. |
| 7,625,764 B2 | 12/2009 | Stayton et al. |
| 7,632,656 B2 | 12/2009 | Kanazawa et al. |
| 7,695,905 B2 | 4/2010 | Furukawa et al. |
| 7,718,193 B2 | 5/2010 | Stayton et al. |
| 7,767,399 B2 | 8/2010 | Murphy et al. |
| 7,981,688 B2 | 7/2011 | Stayton et al. |
| 8,093,026 B2 | 1/2012 | Elaissari et al. |
| 8,110,351 B2 | 2/2012 | Bosnes |
| 8,133,457 B2 | 3/2012 | Ribault et al. |
| 8,137,559 B2 | 3/2012 | Katzke et al. |
| 8,163,886 B2 | 4/2012 | Moya |
| 8,241,591 B2 | 8/2012 | Ribault et al. |
| 8,263,343 B2 | 9/2012 | Hallgren et al. |
| 8,313,902 B2 | 11/2012 | Furukawa et al. |
| 8,362,217 B2 | 1/2013 | Moya et al. |
| 8,499,576 B2 | 8/2013 | Meijer |
| 8,507,283 B2 | 8/2013 | Stayton et al. |
| 8,569,464 B2 | 10/2013 | Moya et al. |
| 8,691,918 B2 | 4/2014 | Jaber et al. |
| 8,877,477 B2 | 11/2014 | Woonton et al. |
| 8,915,374 B2 | 12/2014 | Franks et al. |
| 8,999,702 B2 | 4/2015 | Kelly, Jr. et al. |
| 9,080,933 B2 | 7/2015 | Stayton et al. |
| 9,090,930 B2 | 7/2015 | Ribault et al. |
| 9,174,860 B2 | 11/2015 | Franks et al. |
| 9,217,048 B2 | 12/2015 | Jaber et al. |
| 9,376,464 B2 | 6/2016 | Moya et al. |
| 9,410,181 B2 | 8/2016 | Ribault et al. |
| 9,803,165 B2 | 10/2017 | Moya et al. |
| 2001/0018513 A1 | 8/2001 | Baker |
| 2002/0058786 A1 | 5/2002 | Chivers |
| 2002/0098567 A1 | 7/2002 | Vaidya et al. |
| 2003/0059840 A1 | 3/2003 | Chilkoti |
| 2003/0085228 A1 | 5/2003 | Oakes |
| 2003/0186293 A1 | 10/2003 | Ohnishi et al. |
| 2004/0009473 A1 | 1/2004 | Pease |
| 2004/0010163 A1 | 1/2004 | Hilbrig |
| 2004/0029143 A1 | 2/2004 | Van Ness et al. |
| 2004/0039177 A1 | 2/2004 | Yamanaka et al. |
| 2004/0058436 A1 | 3/2004 | Zhang et al. |

(56) References Cited

U.S. PATENT DOCUMENTS

| | | |
|---|---|---|
| 2004/0062140 A1 | 4/2004 | Cadogan et al. |
| 2004/0134846 A1 | 7/2004 | Akiyama et al. |
| 2004/0185437 A1 | 9/2004 | Hermet et al. |
| 2004/0219628 A1 | 11/2004 | Tashiro et al. |
| 2004/0248774 A1 | 12/2004 | Tayot |
| 2005/0016620 A1 | 1/2005 | Proulx et al. |
| 2005/0063259 A1 | 3/2005 | Isshiki et al. |
| 2005/0158782 A1 | 7/2005 | Furukawa et al. |
| 2005/0158851 A1 | 7/2005 | Furey et al. |
| 2005/0175702 A1 | 8/2005 | Muller-Schulte |
| 2005/0224415 A1 | 10/2005 | Akiyama et al. |
| 2005/0238620 A1 | 10/2005 | Gomer et al. |
| 2005/0272146 A1 | 12/2005 | Hodge et al. |
| 2005/0282169 A1 | 12/2005 | Turner et al. |
| 2006/0121519 A1 | 6/2006 | Patchornik |
| 2006/0162882 A1 | 7/2006 | O'Hara et al. |
| 2006/0189795 A1 | 8/2006 | Van Alstine et al. |
| 2006/0251610 A1 | 11/2006 | Nakahama |
| 2006/0257993 A1 | 11/2006 | McDevitt et al. |
| 2006/0270036 A1 | 11/2006 | Goodwin et al. |
| 2006/0281158 A1 | 12/2006 | Felder et al. |
| 2007/0148437 A1 | 6/2007 | Muller-Schulte |
| 2007/0193954 A1 | 8/2007 | Busson |
| 2007/0224241 A1 | 9/2007 | Stayton et al. |
| 2007/0249737 A1 | 10/2007 | Miller et al. |
| 2007/0298451 A1 | 12/2007 | Ribault et al. |
| 2008/0032396 A1 | 2/2008 | Chokshi |
| 2008/0131957 A1 | 6/2008 | Ryan et al. |
| 2008/0160559 A1 | 7/2008 | Carre et al. |
| 2008/0193981 A1 | 8/2008 | Fahrner et al. |
| 2008/0220531 A1 | 9/2008 | Stayton et al. |
| 2008/0255027 A1 | 10/2008 | Moya et al. |
| 2008/0284163 A1 | 11/2008 | Proulx et al. |
| 2008/0293118 A1 | 11/2008 | Furukawa et al. |
| 2008/0293926 A1 | 11/2008 | Hallgren et al. |
| 2009/0001025 A1 | 1/2009 | Takahashi et al. |
| 2009/0036651 A1 | 2/2009 | Moya |
| 2009/0050566 A1 | 2/2009 | Kozlov et al. |
| 2009/0130704 A1 | 5/2009 | Gyure |
| 2009/0148961 A1 | 6/2009 | Luchini et al. |
| 2009/0155201 A1 | 6/2009 | Mandeville, III et al. |
| 2009/0181450 A1 | 7/2009 | Ribault et al. |
| 2009/0182120 A1 | 7/2009 | Utermohlen et al. |
| 2009/0232737 A1 | 9/2009 | Moya et al. |
| 2009/0233327 A1 | 9/2009 | Lau et al. |
| 2009/0311776 A1 | 12/2009 | Kelly, Jr. et al. |
| 2010/0012589 A1 | 1/2010 | Ribault et al. |
| 2010/0190963 A1 | 7/2010 | Moya et al. |
| 2010/0193148 A1 | 8/2010 | McKay et al. |
| 2010/0200507 A1 | 8/2010 | Kozlov et al. |
| 2010/0209987 A1 | 8/2010 | Elaissari et al. |
| 2010/0215749 A1 | 8/2010 | Stayton et al. |
| 2010/0267933 A1 | 10/2010 | Wilson |
| 2010/0282425 A1 | 11/2010 | Karppi et al. |
| 2011/0020327 A1 | 1/2011 | Moya et al. |
| 2011/0045081 A1 | 2/2011 | Steitz et al. |
| 2011/0065900 A1 | 3/2011 | Johansson et al. |
| 2011/0174735 A1 | 7/2011 | Ribault et al. |
| 2011/0257435 A1 | 10/2011 | Favero et al. |
| 2011/0313066 A1 | 12/2011 | Jaber et al. |
| 2012/0070836 A1 | 3/2012 | Zillmann et al. |
| 2012/0077249 A1 | 3/2012 | Ramaswamy et al. |
| 2012/0283419 A1 | 11/2012 | Thiyagarajan et al. |
| 2013/0005950 A1 | 1/2013 | Moya et al. |
| 2013/0123476 A1 | 5/2013 | Moya |
| 2013/0137860 A1 | 5/2013 | Moya et al. |
| 2014/0171594 A1 | 6/2014 | Jaber et al. |
| 2014/0263011 A1 | 9/2014 | Thiyagarajan et al. |
| 2015/0018440 A1 | 1/2015 | Woonton et al. |
| 2015/0133636 A1 | 5/2015 | Xenopoulos et al. |
| 2015/0218208 A1 | 8/2015 | Koguma et al. |
| 2015/0239956 A1 | 8/2015 | Koguma et al. |
| 2015/0268236 A1 | 9/2015 | Stayton et al. |
| 2015/0291656 A1 | 10/2015 | Hobel et al. |

FOREIGN PATENT DOCUMENTS

| | | | |
|---|---|---|---|
| EP | 0162034 B1 | 11/1990 | |
| EP | 0534016 A1 | 3/1993 | |
| EP | 0420937 B1 | 11/1994 | |
| EP | 0832181 A1 | 4/1998 | |
| EP | 0922715 A2 | 6/1999 | |
| EP | 0851768 B1 | 4/2002 | |
| EP | 1312643 B1 | 5/2005 | |
| EP | 1532243 B1 | 5/2005 | |
| EP | 1201667 B1 | 9/2005 | |
| EP | 1832341 A1 | 9/2007 | |
| EP | 1923461 A1 | 5/2008 | |
| EP | 1312671 B1 | 4/2009 | |
| EP | 1969292 B1 | 3/2011 | |
| EP | 2344517 B1 | 6/2014 | |
| EP | 1928580 B1 | 8/2014 | |
| GB | 2297926 A | 8/1996 | |
| GB | 2305936 A | 4/1997 | |
| JP | 6-116169 A | 4/1994 | |
| JP | 9-12598 A | 1/1997 | |
| JP | 11-505714 A | 5/1999 | |
| JP | 2000-500733 A | 1/2000 | |
| JP | 2000-86729 A | 3/2000 | |
| JP | 2001-517632 A | 10/2001 | |
| JP | 5612761 B2 | 10/2014 | |
| KR | 10-2009-0113264 A | 10/2009 | |
| KR | 10-1551295 B1 | 9/2015 | |
| WO | 91/00360 A1 | 1/1991 | |
| WO | 92/00373 A1 | 1/1992 | |
| WO | 92/20373 A1 | 11/1992 | |
| WO | 93/04173 A1 | 3/1993 | |
| WO | 93/08829 A1 | 5/1993 | |
| WO | 93/14110 A1 | 7/1993 | |
| WO | 93/16185 A2 | 8/1993 | |
| WO | 94/15951 A1 | 7/1994 | |
| WO | 95/06249 A1 | 3/1995 | |
| WO | 95/19181 A1 | 7/1995 | |
| WO | 95/23865 A1 | 9/1995 | |
| WO | 96/02577 A1 | 2/1996 | |
| WO | 96/27011 A1 | 9/1996 | |
| WO | 96/30046 A1 | 10/1996 | |
| WO | 96/37600 A1 | 11/1996 | |
| WO | 96/40210 A1 | 12/1996 | |
| WO | 98/23761 A1 | 6/1997 | |
| WO | 97/26912 A2 | 7/1997 | |
| WO | 98/06248 A2 | 2/1998 | |
| WO | 98/33162 A1 | 7/1998 | |
| WO | 98/45331 A2 | 10/1998 | |
| WO | 98/51793 A1 | 11/1998 | |
| WO | 99/01556 A2 | 1/1999 | |
| WO | 99/15186 A1 | 4/1999 | |
| WO | 99/35500 A1 | 7/1999 | |
| WO | 00/12618 A1 | 3/2000 | |
| WO | 00/46262 A1 | 8/2000 | |
| WO | 00/67901 A1 | 11/2000 | |
| WO | 00/75348 A1 | 12/2000 | |
| WO | 01/07548 A1 | 2/2001 | |
| WO | 01/40309 A2 | 6/2001 | |
| WO | 01/52612 A2 | 7/2001 | |
| WO | 03/101486 A2 | 12/2003 | |
| WO | 2004/056312 A2 | 7/2004 | |
| WO | 2004/092393 A1 | 10/2004 | |
| WO | 2005/010141 A2 | 2/2005 | |
| WO | 2005/021129 A1 | 3/2005 | |
| WO | WO-2005021129 A1 * | 3/2005 | ............... B01D 2/01 |
| WO | 2005/108546 A2 | 11/2005 | |
| WO | 2005/118771 A2 | 12/2005 | |
| WO | 2006/085321 A2 | 8/2006 | |
| WO | 2006/138143 A1 | 12/2006 | |
| WO | 2007/002690 A2 | 1/2007 | |
| WO | 2007/038523 A2 | 4/2007 | |
| WO | 2007/073311 A1 | 6/2007 | |
| WO | 2007/104456 A1 | 9/2007 | |
| WO | 2007/148230 A2 | 12/2007 | |
| WO | 2008/004988 A1 | 1/2008 | |
| WO | 2008/079280 A1 | 7/2008 | |
| WO | 2008/079302 A2 | 7/2008 | |
| WO | 2008/091740 A2 | 7/2008 | |

(56) References Cited

FOREIGN PATENT DOCUMENTS

| | | | |
|---|---|---|---|
| WO | 2008/097154 | A1 | 8/2008 |
| WO | 2009/089570 | A1 | 7/2009 |
| WO | 2009/141664 | A1 | 11/2009 |
| WO | 2009/158606 | A2 | 12/2009 |
| WO | 2010/082894 | A1 | 7/2010 |
| WO | 2014/090838 | A1 | 6/2014 |
| WO | 2014/123484 | A1 | 8/2014 |
| WO | 2014/123485 | A1 | 8/2014 |
| WO | 2014/133458 | A1 | 9/2014 |
| WO | 2014/133459 | A1 | 9/2014 |
| WO | 2014/133460 | A1 | 9/2014 |

OTHER PUBLICATIONS

Biotechnology and Bioengineering, vol. 60, No. 5, Dec. 1998, pp. 568-579, "Preparation of a New Thermo-Responsive Adsorbent with Maltose as a Ligand and Its Application to Affinity Precipitation", Hoshino, et al.

Transplantation, vol. 58, No. 3, 1994, pp. 377-380, "Administration of an anti-CD11a monoclonal antibody in recipients of kidney transplantation. A pilot study", Hourmant, et al.

Biotechnology Techniques, vol. 4, No. 1, 1990, pp. 55-60, "The Flocculation of Bacteria Using Cationic Synthetic Flocculants and Chitosan", Hughes, et al.

Bioseparation, vol. 7, No. 4-5, 1999, pp. 207-220, "Polycomplexes—potential for bioseparation", Izumrudov, et al.

Proc. Natl. Acad. Sci. USA, vol. 90, Mar. 1993, pp. 2551-2555, "Analysis of homozygous mutant chimeric mice: Deletion of the immunoglobulin heavy-chain joining region blocks B-cell development and antibody production", Jakobovits, et al.

Nature, vol. 362, Mar. 1993, pp. 255-258, "Germ-line transmission and expression of a human-derived yeast artificial chromosome", Jakobovits, et al.

Nature, vol. 321, May 1986, pp. 522-525, "Replacing the complementarity-determining regions in a human antibody with those from a mouse", Jones, et al.

Cancer Research (Suppl.), vol. 55, Dec. 1995, pp. 5908s-5910s, "Radiolabeled Anti-CD33 Monoclonal Antibody M195 for Myeloid Leukemias", Jurcic, et al.

Cancer Research (Suppl.), vol. 55, Dec. 1995, pp. 5899s-5907s, "Treatment of Non-Hodgkin's Lymphoma with Radiolabeled Murine, Chimeric, or Humanized LL2, an Anti-CD22 Monoclonal Antibody", Juweid, et al.

Biotechnology and Bioengineering, vol. 40, No. 11, Dec. 1992, pp. 1381-1387, "Purification of Recombinant Protein A by Aqueous Two-Phase Extraction Integrated with Affinity Precipitation", Kamihira, et al.

Anal. Chem., vol. 69, No. 5, 1997, pp. 823-830, "Temperature-Responsive Liquid Chromatography. 2. Effects of Hydrophobic Groups in N-isopropylacrylamide Copolymer-modified Silica", Kanazawa, et al.

Journal of Chromatography A, vol. 1106, Feb. 2006, pp. 152-158, "Temperature-responsive stationary phase utilizing a polymer of proline derivative for hydrophobic interaction chromatography using an aqueous mobile phase", Kanazawa, et al.

Biochemical Engineering Journal, vol. 40, No. 3, 2008, pp. 512-519, "Flocculation enhanced microfiltration of *Escherichia coli* lysate", Karim, et al.

Journal of Membrane Science, vol. 182, No. 1-2, Feb. 2001, pp. 161-172, "Flocculation to enhance microfiltration", Kim, et al.

Flocculation in Biotechnology and Separation Systems, 1987, pp. 429-439, "Removal of Cell and Cell Debris by Electrostatic Adsorption of Positively Charged Polymeric Particles", Kim, et al.

Growth Factors, vol. 7, 1992, pp. 53-64, "The Vascular Endothelial Growth Factor Proteins: Identification of Biologically Relevant Regions by Neutralizing Monoclonal Antibodies", Kim, et al.

The Journal of Immunology, pp. 2453-2455, Reprinted with permission from Nature, vol. 256 (5517): 495-497 (1975), "Continuous cultures of fused cells secreting antibody of predefined specificity", Kohler, et al.

The Journal of Immunology, vol. 148, No. 5, 1992, pp. 1547-1553, "Formation of a bispecific antibody by the use of leucine zippers", Kostelny, et al.

The Journal of Immunology, vol. 133, No. 6, 1984, pp. 3001-3005, "A human hybrid myeloma for production of human monoclonal antibodies", Kozbor, et al.

Isolation and Purification of Proteins, 2003, edited by Rajni Hatti-Kaul, et al., pp. 237-275, "Precipitation of Proteins", Kumar, et al.

Biotechnology and Bioengineering, vol. 59, Issue 6, 1998, pp. 695-704, "Affinity Precipitation of Amylase Inhibitor from Wheat Meal by Metal Chelate Affinity Binding Using Cu(II)-Loaded Copolymers of 1-Vinylimidazole with N-Isopropylacrylamide", Kumar, et al.

Prog. Polym. Sci., vol. 32, 2007, pp. 1205-1237, "Smart polymers: Physical forms and bioengineering applications", Kumar, et al.

Biotechnology and Bioengineering, vol. 75, No. 5, Dec. 2001, pp. 570-580, "Type-Specific Separation of Animal Cells in Aqueous Two-Phase Systems Using Antibody Conjugates with Temperature-Sensitive Polymers", Kumar, et al.

Am Chem Society, ACS Symposium Series, vol. 362, Chapter 7, 1988, pp. 72-101, "Scale-Up of Bioseparations for Microbial and Biochemical Technology", Ladisch, et al.

Nature, vol. 227, No. 5259, Aug. 1970, pp. 680-685, "Cleavage of Structural Proteins during the Assembly of the Head of Bacteriophage T4", Laemmli.

Bioseparation, vol. 7, 1999, pp. 195-205, "Carboxymethyl cellulose as a new heterobifunctional ligand carrier for affinity precipitation of proteins", Lali, et al.

Journal of Biotechnology, vol. 49, No. 1-3, Aug. 1996, pp. 189-199, "Evaluation of affinity precipitation and a traditional affinity chromatographic precedure for purification of soybean lectin, from extracts of soya flour", Larsson, et al.

Journal of Pharmaceutical Sciences, vol. 100, No. 7, Jul. 2011, pp. 2551-2562, "Assessment of Net Charge and Protein-Protein Interactions of Different Monoclonal Antibodies", Lehermayr, et al.

AIChE Journal, vol. 55, No. 8, Aug. 2009, pp. 2070-2080, "Effect of Molecular Weight of Poly(N-isopropylacrylamide) Temperature-Sensitive Flocculants on Dewatering", Li, et al.

European Journal of Immunology, vol. 26, No. 1, Jan. 1996, pp. 1-9, "Antibody-targeted superantigen therapy induces tumor-infiltrating lymphocytes, excessive cytokine production, and apoptosis in human colon carcinoma", Litton, et al.

The Journal of Immunology, vol. 156, No. 4, 1996, pp. 1646-1653, "In Vivo Blockade of TNF-alpha by Intravenous Infusion of a Chimeric Monoclonal TNF-alpha Antibody in Patients with Rheumatoid Arthritis. Short Term Cellular and Molecular Effects", Lorenz, et al.

Journal of Chromatography B, vol. 878, No. 9-10, Mar. 2010, pp. 798-806, "Using precipitation by polyamines as an alternative to chromatographic separation in antibody purification processes", Ma, et al.

Innovative Food Science and Emerging Technologies, 2007, pp. 1-11, "Novel chromatographic separation—The potential of smart polymers", Maharjan, et al.

Analytical Chemistry, vol. 75, No. 13, Jul. 2003, pp. 2943-2949, "A Smart Microfluidic Affinity Chromatography Matrix Composed of Poly(N-isopropylacrylamide)-Coated Beads", Malmstadt, et al.

Bioconjugate Chem., 2003, vol. 14, No. 3, pp. 575-580, "Affinity Thermoprecipitation and Recovery of Biotinylated Biomolecules via a Mutant Streptavidin-Smart Polymer Conjugate", Malmstadt, et al.

Journal of Molecular Biology, vol. 222,, No. 3, Dec. 1991, pp. 581-597, "By-passing Immunization-Human Antibodies from V-gene Libraries Displayed on Phage", Marks, et al.

Bio/Technology, Nature Publishing Group, vol. 10, Jul. 1992, pp. 779-783, "By-Passing Immunization: Building High Affinity Human Antibodies by Chain Shuffling", Marks, et al.

Nature, vol. 348, Dec. 1990, pp. 552-554, "Phage antibodies: filamentous phage displaying antibody variable domains", McCafferty, et al.

Millipore Pure Science Laboratory Catalogue 1999/2000, Ultrafiltration Discs and Stirred Cells, p. 127, "Solvent-resistant Stirred Cells" and "High-Output Stirred Cells", 3 pages.

(56) References Cited

OTHER PUBLICATIONS

Nature, vol. 305, Oct. 1983, pp. 537-540, "Hybrid hybridomas and their use in immunohistochemistry", Milstein, et al.
Journal of Biochemical and Biophysical Methods, vol. 24, 1992, pp. 107-117, "Single-step purification of F(ab')sub.2 fragments of mouse monoclonal antibodies (immunoglobulins G1) by hydrophobic interaction high performance liquid chromatography using TSKgel Phenyl-5PW", Morimoto, et al.
Proc. Natl. Acad. Sci. USA, vol. 81, Nov. 1984, pp. 6851-6855, "Chimeric human antibody molecules: Mouse antigen-binding domains with human constant region domains", Morrison, et al.
American Inst. of Chem. Engineers, Biotechnology Progress, V 26, No. 5, (2010), pp. 1322-1331, "Monoclonal Antibody Purification Using Cationic Polyelectrolytes: An Alternative to Column Chromatography", Peram, et al.
Flocculation in Biotechnology and Separation Systems, 1987, pp. 457-466, "Flocculation of Cell Debris for Improved Separation by Centrifugation", Persson, et al.
The Journal of Immunology, vol. 151, No. 5, Sep. 1993, pp. 2623-2632, "Humanization of an Antibody Directed Against IgE", Presta, et al.
Current Opinion in Structural Biology, vol. 2, No. 4, Aug. 1992, pp. 593-596, "Antibody Engineering", Presta.
Cancer Research (Suppl.), vol. 55, Dec. 1995, pp. 5916s-5920s, "Radioimmunotherapy for Breast Cancer Using Escalating Fractionated Doses of 131-I-labeled Chimeric L6 Antibody with Peripheral Blood Progenitor Cell Transfusions", Richman, et al.
Nature, vol. 332, Mar. 1988, pp. 323-327, "Reshaping human antibodies for therapy", Riechmann, et al.
Journal of Biotechnology, vol. 128, No. 4, Mar. 2007, pp. 813-823, "The use of chitosan as a flocculant in mammalian cell culture dramatically improves clarification throughput without adversely impacting monoclonal antibody recovery", Riske, et al.
Biotechnol. Prog, vol. 24, No. 3, May/Jun. 2008, pp. 488-495, "Advances in Primary Recovery: Centrifugation and Membrane Technology", Roush, et al.
Anal. Chem., vol. 71, No. 20, Oct. 1999, pp. 4506-4512, "Concentration of Hydrophobic Organic Compounds by Polymer-Mediated Extraction", Saitoh, et al.
Kona, No. 20, 2002, pp. 246-250, "Flocculation Mechanism of Suspended Particles Using the Hydrophilic/Hydrophobic Transition of a Thermosensitive Polymer", Sakohara, et al.
Advanced Drug Delivery Reviews, vol. 58, No. 15, 2006, pp. 1655-1670, "Thermo-and pH-responsive polymers in drug delivery", Schmaljohann.
The Journal of Physical Chemistry B, vol. 111, No. 29, 2007, pp. 8649-8654, "Cationic Flocculants Carrying Hydrophobic Functionalities: Applications for Solid/Liquid Separation", Schwarz, et al.
Biotechnology and Bioengineering, vol. 34, No. 3, 1989, pp. 387-393, "Purification of Wheat Germ Agglutinin Using Affinity Flocculation with Chitosan and a Subsequent Centrifugation or Flotation Step", Senstad, et al.
Macromolecules, American Chemical Society, vol. 24, No. 15, 1991, pp. 4255-4263, "Self-organization of Poly (allylamine)s Containing Hydrophobic Groups and Its Effect on the Interaction with Small Molecules. 1. Static Fluorometry", Seo, et al.
J. Exp. Med., vol. 175, 1992, pp. 217-225, "Development of Humanized Bispecific Antibodies Reactive with Cytotoxic Lymphocytes and Tumor Cells Overexpressing the HER2 Protooncogene", Shalaby, et al.
Journal of Biotechnology, vol. 49, 1996, pp. 173-178, "Flocculation of cell, cell debris and soluble protein with methacryloyloxyethyl trimethylammonium chloride-acrylonitrile copolymer", Shan, et al.
Cancer Research (Suppl.), vol. 55, Dec. 1995, pp. 5935s-5945s, "Evaluation of a Complementarity-Determining Region-Grafted (Humanized) Anti-Carcinoembryonic Antigen Monoclonal Antibody in Preclinical and Clinical Studies", Sharkey, et al.
The Journal of Immunology, vol. 151, No. 4, 1993, pp. 2296-2308, "A Humanized CD18 Antibody Can Block Function Without Cell Destruction", Sims, et al.
Chest, vol. 103, No. 3, Mar. 1993, pp. 932-943, "Immunologic Therapy for ARDS, Septic Shock, and Multiple-Organ Failure", St. John, et al.
Cell, vol. 66, No. 6, 1991, pp. 1133-1144, "The B Lymphocyte Adhesion Molecule CD22 Interacts with Leukocyte Common Antigen CD45RO on T Cells and a2-6 Sialyltransferase, CD75, on B Cells", Stamenkovic, et al.
The Affinity Precipitation for the Isolation of Biomolecules, No. 3862, Aug. 2007, pp. 1-130, 146 pages, Stockermajd, et al, submitted in two parts.
Transplant International, vol. 4, No. 1, 1991, pp. 3-7, "Anti-LFA1 monoclonal antibody (25.3) for treatment of steroid-resistant grade III-IV acute graft-versus-host disease", Stoppa, et al.
Journal of Chromatography A, vol. 1114, 2006, pp. 239-249, "Temperature sensitive dopamine-imprinted (N,N-methylene-bis-acrylamide cross-linked) polymer and its potential application to the selective extraction of adrenergic drugs from urine", Suedee, et al.
Analytical Sciences, vol. 3, No. 6, Dec. 1987, pp. 479-488, "Ion-Association Reagents, A Review", Toei.
The EMBO Journal, vol. 10, No. 12, 1991, pp. 3655-3659, "Bispecific single chain molecules (Janusins) target cytotoxic lymphocytes on HIV infected cells", Traunecker, et al.
The Journal of Immunology, vol. 147, No. 1, Jul. 1991, pp. 60-69, "Trispecific F(ab')3 derivatives that use cooperative signaling via the TCR/CD3 complex and CD2 to activate and redirect resting cytotoxic T cells", Tutt, et al.
Flocculation in Biotechnology and Separation Systems, 1987, pp. 351-368, "Aspects of Bioflocculation: An Overview", Unz.
Nature Biotechnology, vol. 14, 1996, pp. 309-314, "Human Antibodies with Sub-nanomolar Affinities Isolated from a Large Non-immunized Phage Display Library", Vaughan, et al.
Science, vol. 239, Mar. 1988, pp. 1534-1536, "Reshaping Human Antibodies: Grafting an Antilysozyme Activity", Verhoeyen, et al.
Nucleic Acids Research, vol. 21, No. 9, 1993, pp. 2265-2266, "Combinatorial infection and in vivo recombination: a strategy for making large phage antibody repertoires", Waterhouse, et al.
Biotechnology and Bioengineering, vol. 108, No. 1, Jan. 2011, pp. 50-58, "Effects of Solution Environment on Mammalian Cell Fermentation Broth Properties: Enhanced Impurity Removal and Clarification Performance", Westoby, et al.
Biotechnology and Bioengineering, vol. 86, No. 6, 2004, pp. 612-621, "Clearance of Minute Virus of Mice by Flocculation and Microfiltration", Wickramasinghe, et al.
Desalination, vol. 147, No. 1-3, 2002, pp. 25-30, "Enhanced microfiltration of yeast by flocculation", Wickramasinghe, et al.
Separation Science and Technology, vol. 37, No. 1, pp. 217-228, 2002, "Selective Precipitation of Water-Soluble Proteins Using Designed Polyelectrolyte", Yu, et al.
Protein Engineering, vol. 8, No. 10, 1995, pp. 1057-1062, "Engineering linear F(ab')2 fragments for efficient production in *Escherichia coli* and enhanced antiproliferative activity", Zapata, et al.
Nucleic Acids Research, vol. 31, No. 13, 2003, pp. 3406-3415, "Mfold web server for nucleic acid folding and hybridization prediction", Zuker.
International Search Report mailed Mar. 31, 2008 in corresponding PCT application No. PCT/US2007/26040.
International Search Report dated Apr. 24, 2008 in corresponding PCT application No. PCT/US2007/26090.
International Search Report dated Aug. 27, 2009 in corresponding PCT application No. PCT/US2008/013736.
International Search Report dated Feb. 18, 2010 in co-pending PCT application No. PCT/US2009/006363.
International Search Report/Written Opinion dated Dec. 6, 2011 in co-pending PCT application No. PCT/US2011/039595.
International Search Report dated Oct. 31, 2011 in co-pending PCT application No. PCT/US2011/036648.
Office Action mailed Jun. 21, 2011 in corresponding U.S. Appl. No. 12/316,708.
Office Action mailed Feb. 29, 2012 in corresponding U.S. Appl. No. 12/316,708.
Final Rejection mailed Sep. 25, 2012 in corresponding U.S. Appl. No. 12/316,708.

(56) References Cited

OTHER PUBLICATIONS

Office Action-Restriction-mailed Feb. 7, 2012 in corresponding U.S. Appl. No. 12/448,004.
Office Action mailed Jul. 26, 2012 in corresponding U.S. Appl. No. 12/448,004.
Office Action-Restriction-mailed Apr. 27, 2012 in co-pending U.S. Appl. No. 12/592,744.
Office Action Feb. 21, 2012 in co-pending U.S. Appl. No. 12/387,688.
Office Action-Restriction-mailed Jul. 17, 2012 in co-pending U.S. Appl. No. 12/633,141.
Office Action mailed Jan. 31, 2013 in co-pending U.S. Appl. No. 12/633,141.
Office Action mailed Feb. 22, 2013 in co-pending U.S. Appl. No. 13/610,954.
Office Action mailed Mar. 15, 2013 in co-pending U.S. Appl. No. 13/108,576.
Final Rejection mailed Dec. 28, 2012 in co-pending U.S. Appl. No. 12/387,688.
Office Action-Rejection mailed Nov. 21, 2012 in co-pending U.S. Appl. No. 13/155,912.
Notice of Allowance mailed Oct. 31, 2013 in co-pending U.S. Appl. No. 13/610,954.
Final Rejection mailed Oct. 22, 2013 in co-pending U.S. Appl. No. 13/108,576.
Protein Expression and Purification, vol. 7, Article No. 0042, 1996, pp. 294-298, "Sequential Precipitation with Reversibly Soluble Insoluble Polymers as a Bioseparation Strategy: Purification of B-Glucosidase from *Trichoderma longibrachiatum*", Agarwal, et al.
Journal of Chromatography B, vol. 761, No. 2, 2001, pp. 247-254, "New antibody purification procedure using a thermally responsive poly(N-isopropylacrylamide)-dextran derivative conjugate", Anastase-Ravion, et al.
Cell, vol. 61, No. 7, Jun. 1990, pp. 1303-1313, "CD44 is the Principal Cell Surface Receptor for Hyaluronate", Aruffo, et al.
Process Technology Proceedings, vol. 4, Proceedings of the International Symposium on Flocculation in Biotechnology and Separations Systems, San Francisco, California, Jul. 28-Aug. 1, 1986, pp. 429 & 441, "Flocculation in Biotechnology and Separation Systems", Attia.
Journal of Chromatography A, vol. 1119, 2006, pp. 58-65, "Aqueous chromatography system using pH- and temperature-responsive stationary phase with ion-exchange groups", Ayano, et al.
Science, vol. 229, Jul. 1985, pp. 81-83, "Preparation of Bispecific Antibodies by Chemical Recombination of Monoclonal Immunoglobulin G1 Fragments", Brennan, et al.
Monoclonal Antibody Production Techniques and Application, pp. 51-63 (Marcel Dekker, Inc., New York 1987), "Mouse-Human Myeloma Partners for the Production of Heterohybridomas", Brodeur, et al.
The Year in Immunology, vol. 7, 1993, pp. 33-40, "Designer Mice: The Production of Human Antibody Repertoires in Transgenic Animals", Bruggemann, et al.
Bio/Technology, Nature Publishing Group, vol. 10, Feb. 1992, pp. 163-167, "High Level *Escherichia coli* Expression and Production of a Bivalent Humanized Antibody Fragment", Carter, et al.
Macromolecular Bioscience, vol. 5, No. 5, 2005, pp. 373-378, "Highly Branched Stimuli Responsive Poly[(N-isopropylacrylamide)-co-(1,2-propandiol-3-methacrylate)]s with Protein Binding Functionality", Carter, et al.
Proc. Natl. Acad. Sci. USA, vol. 89, May 1992, pp. 4285-4289, "Humanization of an anti-p185HER2 antibody for human cancer therapy", Carter, et al.
"Technology: Temperature-responsive polymers", document retrieved on Oct. 13, 2010, available at: http://www.cellseed.com/technology-e/indexhtml, 1 page, Cellseed, Inc.
Cancer Research (Suppl.), vol. 55, Dec. 1, 1995, pp. 5852s-5856s, "Biological Activity of Two Humanized Antibodies against Two Different Breast Cancer Antigens and Comparison to Their Original Murine Forms", Ceriani, et al.

Macromolecular Chemistry and Physics, vol. 196, No. 4, Apr. 1995, pp. 1251-1259, "A new temperature- and pH-responsive copolymer for possible use in protein conjugation", Chen, et al.
Nature, vol. 373, No. 5, Jan. 1995, pp. 49-52, "Graft copolymers that exhibit temperature-induced phase transitions over a wide range of pH", Chen, et al.
Langmuir, vol. 21, No. 25, 2005, pp. 11673-11677, "pH-Dependence of the Properties of Hydrophobically Modified Polyvinylamine", Chen, et al.
Biomaterials, vol. 11, No. 9, Nov. 1990, pp. 631-633, "Polymer-protein conjugates. II. Affinity precipitation separation of human immunogammaglobulin by a poly (N-isopropylacrylamide)-protein A conjugate", Chen, et al.
Colloids and Surfaces B: Biointerfaces, vol. 6, 1996, pp. 37-49, "Characterization of pH-sensitive polymeric supports for selective precipitation of proteins", Chern, et al.
Journal of Molecular Biology, vol. 196, 1987, pp. 901-917, "Canonical Structures for the Hypervariable Regions of Immunoglobulins", Chothia, et al.
Arthritis & Rheumatism, vol. 39, No. 1, Jan. 1996, pp. 52-56, "Percentage of anti-CD4 monoclonal antibody-coated lymphocytes in the rheumatoid joint is associated with clinical improvement. Implications for the development of immunotherapeutic dosing regimens", Choy, et al.
Nature, vol. 352, Aug. 1991, pp. 624-628, "Making antibody fragments using phage display libraries", Clackson, et al.
Bioseparation, vol. 7, No. 4-5, Jul. 1999, pp. 231-240, "Affinity precipitation of monoclonal antibodies by nonstoichiometric polyelelectrolyte complexes", Dainiak, et al.
Journal of Colloid and Interface Science, vol. 179, No. 1, 1996, pp. 188-193, "Temperature-Sensitive Flocculants Based on Poly (N-isopropylacrylamide-co-diallyldimethylammonium Chloride)", Deng, et al.
Critical Care Medicine, vol. 23, No. 9, Sep. 1995, pp. 1461-1469, "CDP571, a humanized antibody to human tumor necrosis factor-alpha: Safety, pharmacokinetics, immune response, and influence of the antibody on cytokine concentrations in patients with septic shock", Dhainaut, et al.
Nature, vol. 411, May 2001, pp. 59-62, "Size-dependent control of the binding of biotinylated proteins to streptavidin using a polymer shield", Ding, et al.
Nature, vol. 355, Jan. 1992, pp. 258-262, "Immunization of hu-PBL-SCID mice and the rescue of human monoclonal Fab fragments through combinatorial libraries", Duchosal, et al.
Journal of Polymer Science, vol. XIII, No. 6, Feb. 1954, pp. 85-91, "Viscosities of Dilute Aqueous Solutions of a Partially Quaternized Poly-4-vinylpyridine at Low Gradients of Flow", Eisenberg, et al.
The Journal of Immunology, vol. 155, No. 2, 1995, pp. 925-937, "Engineered Anti-CD38 Monoclonal Antibodies for Immunotherapy of Multiple Myeloma", Ellis, et al.
Flocculation in Biotechnology and Separation Systems, 1987, pp. 441-455, "Flocculation of *E. coli* Bacteria With Cationic Polyelectrolytes", Eriksson, et al.
Flocculation in Biotechnology and Separation Systems, 1987, pp. 383-398, "Genetic Control of Flocculation of Yeast With Respect to Application in Biotechnology", Esser, et al.
Journal of Chromatography A, vol. 1195, 2008, pp. 94-100, "Purification of human immunoglobulin G by thermoseparating aqueous two-phase systems", Ferriera, et al.
Biotechnology and Bioengineering, vol. 79, No. 3, Aug. 5, 2002, pp. 271-276, "Affinity Separation Using an Fv Antibody Fragment-"Smart" Polymer Conjugate", Fong, et al.
Bioconjugate Chem., vol. 10, No. 5, 1999, pp. 720-725, "Thermoprecipitation of Streptavidin via Oligonucleotide-Mediated Self-Assembly with Poly (N-isopropylacrylamide)", Fong, et al.
Chimia 55, No. 3, 2001, pp. 196-200, "Stimulus-Responsive Polymers for Bioseparation", Freitag, et al.
Trends in Biotechnology, vol. 9, No. 6, Jun. 1991, pp. 191-196, "Application of reversibly soluble polymers in bioprocessing", Fujii, et al.
Trends in Biotechnology, vol. 17, No. 8, Aug. 1999, pp. 335-340, "'Smart' polymers and what they could do in biotechnology and medicine", Galaev, et al.

(56) References Cited

OTHER PUBLICATIONS

Russian Chemical Reviews, vol. 64, No. 5, 1995, pp. 471-489, "'Smart' polymers in biotechnology and medicine", Galaev.
Journal of Chromatography A, vol. 684, 1994, pp. 45-54, "Interaction of Cibacron Blue with polymers: implications for polymer-shielded dye-affinity chromatography of phosphofructokinase from baker's yeast", Galaev, et al.
Biotechnology and Bioengineering, vol. 71, No. 3, 2000/2001, pp. 223-234, "Use of the Avidin (Imino)biotin System as a General Approach to Affinity Precipitation", Garret-Flaudy, et al.
Process Biochemistry, vol. 34, No. 6-7, Sep. 1999, pp. 577-580, "Purification of *Aspergillus* sp xylanase by precipitation with an anionic polymer Eudragit S 100", Gawande, et al.
Progress in Polymer Science, vol. 29, No. 12, Dec. 2004, pp. 1173-1222, "Stimuli-responsive polymers and their bioconjugates", Gil, et al.
Monoclonal Antibodies: Principles and Practice, Academic Press, 1986, pp. 59-103, "3. Production of Monoclonal Antibodies", Goding.
The Journal of Immunology, vol. 155, No. 10, 1995, pp. 4996-5002, "Construction and Characterization of a Humanized Anti-gamma-Ig Receptor Type I (Fc gamma RI) Monoclonal Antibody", Graziano, et al.
The Journal of Immunology, vol. 152, No. 11, 1994, pp. 5368-5374, "Efficient Tumor Cell Lysis Mediated by a Bispecific Single Chain Antibody Expressed in *Escherichia coli*", Gruber, et al.
Bioseparation, vol. 5, 1995, pp. 339-350, "Alternative modes of precipitation of Eudragit S-100: a potential ligand carrier for affinity precipitation of protein", Guoqiang, et al.
Journal of Molecular Recognition, vol. 9, 1996, pp. 356-359, XP-002538983, "Affinity Precipitation of Proteins", Gupta, et al.
Am Inst. of Chem Engineers Journal, Jul. 2003, vol. 49, No. 7, pp. 1687-1701, "Flocculation of Biological Cells: Experiment vs. Theory", Han, et al.
Analyst, vol. 129, 2004, pp. 421-427, "Capturing of acidic macromolecules from biological samples using a temperature-responsive polymer modified with poly-L-lysine", Hayashi, et al.
Journal of Chromatography B, vol. 790, Jun. 2003, pp. 79-90, "Protein purification by affinity precipitation", Hilbrig, et al.
The Proceedings of the National Academy of Sciences, USA, vol. 90, No. 14, Jul. 1993, pp. 6444-6448, "'Diabodies': Small bivalent and bispecific antibody fragments", Holliger, et al.
International Search Report and Written opinion dated Jan. 29, 2010 in co-pending PCT application No. PCT/US09/67097, 8 pages.
International Preliminary Report on Patentability mailed Jun. 30, 2011 in co-pending PCT Patent Application No. PCT/US2009/067097, 7 pages.
Extended European Search Report mailed Nov. 17, 2009 in co-pending EP Patent Application No. 09161982.5, 6 pages.
International Search Report/Written Opinion mailed Nov. 12, 2009 in co-pending PCT Patent Application No. PCT/US2009/002787, 9 pages.
International Preliminary Report on Patentability issued Dec. 13, 2010 in co-pending PCT Patent Application No. PCT/US2009/002787, 6 pages.
Office Action dated Nov. 17, 2010 in co-pending U.S. Appl. No. 12/387,688.
Final Rejection dated Apr. 21, 2011 in co-pending U.S. Appl. No. 12/387,688.
Merriam Webster Dictionary, accessed May 14, 2013 at http://www.merriam-webster.com/dictionary/associated, Definition of the word "associate . . . " 6 pages.
Restriction mailed May 9, 2013 in corresponding U.S. Appl. No. 13/747,495.
Office Action mailed Apr. 30, 2013 in co-pending U.S. Appl. No. 13/155,912.
Office Action mailed Apr. 15, 2013 in co-pending U.S. Appl. No. 12/108,576.
International Preliminary Report on Patentability mailed Jun. 30, 2011 in co-pending PCT application No. PCT/US2009/006363.
International Preliminary Report on Patentability mailed Nov. 29, 2012 in co-pending PCT application No. PCT/US2011/036648.
International Preliminary Report on Patentability mailed Dec. 20, 2012 in co-pending PCT application No. PCT/US2011/039595.
Final Rejection mailed Jun. 25, 2013 in co-pending U.S. Appl. No. 12/633,141.
Notice of Allowance mailed Aug. 21, 2013 in corresponding U.S. Appl. No. 12/316,708.
Final Rejection mailed Aug. 19, 2013 in co-pending U.S. Appl. No. 12/387,688.
French Search Report dated Jun. 2, 2009 in co-pending French patent application No. FA 713810/FR 0854844.
Office Action mailed Feb. 26, 2009 in co-pending U.S. Appl. No. 11/805,539.
Office Action mailed May 26, 2009 in co-pending U.S. Appl. No. 11/805,539.
Office Action mailed Jul. 30, 2009 in co-pending U.S. Appl. No. 11/805,539.
Final Rejection mailed Dec. 29, 2009 in co-pending U.S. Appl. No. 11/805,539.
Final Rejection mailed Apr. 20, 2010 in co-pending U.S. Appl. No. 11/805,539.
Final Rejection mailed Aug. 27, 2010 in co-pending U.S. Appl. No. 12/805,539.
Final Rejection mailed Jan. 7, 2011 in co-pending U.S. Appl. No. 11/805,539.
Office Action mailed Apr. 21, 2011 in co-pending U.S. Appl. No. 11/805,539.
Final Rejection mailed Oct. 18, 2011 in co-pending U.S. Appl. No. 11/805,539.
Advisory Action mailed Nov. 25, 2011 in co-pending U.S. Appl. No. 11/805,539.
Examiner's Answer to Appeal Brief mailed Jul. 3, 2012 in co-pending U.S. Appl. No. 11/805,539.
Office Action mailed Nov. 1, 2011 in co-pending U.S. Appl. No. 12/383,131.
Final Rejection mailed Apr. 13, 2012 in co-pending U.S. Appl. No. 12/383,131.
Office Action mailed Jun. 11, 2013 in co-pending U.S. Appl. No. 12/383,131.
Final Rejection mailed Oct. 24, 2013 in co-pending U.S. Appl. No. 12/383,131.
Office Action mailed Feb. 4, 2014 in co-pending U.S. Appl. No. 12/383,131.
Office Action mailed Feb. 27, 2014 in co-pending U.S. Appl. No. 12/387,688.
Office Action mailed Apr. 3, 2014 in co-pending U.S. Appl. No. 12/633,141.
Biotechnol. Appl. Biochem. (1999), vol. 30, pp. 235-244, "Expression system for foreign genes using the fission yeast *Schizosaccharomyces pombe*", Giga-Hama, et al.
European Search Report mailed Jul. 9, 2013 in co-pending European Patent Application No. EP 09835506.8.
Office Action mailed Nov. 25, 2013 in corresponding U.S. Appl. No. 13/747,495.
Notice of Allowance mailed Nov. 22, 2013 in co-pending U.S. Appl. No. 13/108,576.
Final Rejection dated Jun. 23, 2014 in co-pending U.S. Appl. No. 12/383,131.
Journal of the Chemical Society of Japan, No. 8, Aug. 1991, pp. 1115-1126 (English Abstract Submitted), "Structure and Hydrolysis Activity of Poly(alylamine)s having Hydrophobic Groups", Seo, et al.
Office Action dated Dec. 19, 2014 in co-pending U.S. Appl. No. 12/383,131.
Notice of Allowance dated Jun. 4, 2015 in co-pending U.S. Appl. No. 12/383,131.
Final Rejection dated Jul. 27, 2015 in co-pending U.S. Appl. No. 12/633,141.
Final Rejection dated Aug. 8, 2014 in corresponding U.S. Appl. No. 13/747,495.
Office Action dated Jul. 29, 2014 in co-pending U.S. Appl. No. 12/387,688.

(56) References Cited

OTHER PUBLICATIONS

Final Rejection dated Aug. 14, 2014 in co-pending U.S. Appl. No. 12/633,141.
Office Action-Restriction-dated Sep. 30, 2014 in corresponding U.S. Appl. No. 13/732,613.
Notice of Allowance dated Nov. 14, 2014 in co-pending U.S. Appl. No. 13/610,954.
Japanese communication, with English translation, dispatched Sep. 2, 2014 in co-pending Japanese patent application No. 2013-083213.
Office Action dated Mar. 16, 2015 in corresponding U.S. Appl. No. 13/732,613.
Office Action dated Mar. 2, 2015 in co-pending U.S. Appl. No. 12/633,141.
Notice of Allowance dated Feb. 20, 2015 in co-pending U.S. Appl. No. 12/387,688.
Final Rejection dated Oct. 20, 2015 in co-pending U.S. Appl. No. 13/732,613.
Office Action dated Sep. 17, 2015 in co-pending U.S. Appl. No. 13/747,495.
Notice of Allowance dated Oct. 20, 2015 in co-pending U.S. Appl. No. 13/610,954.
Majd, Gisela S., "The affinity precipitation for the isolation of biomolecules" Thèse EPFL, No. 3862, pp. 1-130, Aug. 2007.
International Preliminary Report on Patentability dated Jun. 24, 2009 in co-pending PCT application No. PCT/US2007/026040.
International Preliminary Report on Patentability dated Jun. 24, 2009 in co-pending PCT application No. PCT/US2007/026090.
International Preliminary Report on Patentability dated Jun. 22, 2010 in co-pending PCT application No. PCT/US2008/013736.
Notice of Allowance dated Feb. 10, 2016 in co-pending U.S. Appl. No. 11/805,539.
Notice of Allowance dated Mar. 2, 2016 in co-pending U.S. Appl. No. 13/747,495.
Final rejection dated Feb. 25, 2016 in co-pending U.S. Appl. No. 12/633,141.
Japanese communication, with English translation, dated Jul. 19, 2016 in co-pending Japanese patent application No. 2015-215483.
Final rejection dated May 2, 2017 in co-pending U.S. Appl. No. 13/732,613.
Hemstrom et al., "Hydrophilic Interaction Chromatography," Journal of Separation Science, vol. 29, Iss.12, pp. 1784-1821, Aug. 2006.
Nisnevitch et al., "The Solid Phase in Affinity Chromatography: Strategies for Antibody Attachment," Journal of Biochemical and Biophysical Methods, vol. 49, pp. 467-480, Oct. 30 2001.
Wang, "Ion Exchange in Purification," Separation Processes in Biotechnology, pp. 359-400, 1990.
Final rejection dated Jan. 27, 2017 in co-pending U.S. Appl. No. 12/633,141.
Advisory action dated Apr. 27, 2017 in co-pending U.S. Appl. No. 12/633,141.
Chiang et al., "Application of Superparamagnetic Nanoparticles in Purification of Plasmid DNA from Bacterial Cells," Journal of Chromatography B, vol. 822, pp. 54-60, Aug. 5, 2005.
Office action dated Oct. 11, 2016 in co-pending U.S. Appl. No. 13/732,613.
Office action dated Oct. 5, 2016 in co-pending U.S. Appl. No. 14/940,864.
Office action dated Sep. 21, 2016 in co-pending U.S. Appl. No. 12/633,141.
Notice of Allowance dated Sep. 15, 2016 in co-pending U.S. Appl. No. 13/610,954.
Notice of Allowance dated Sep. 29, 2016 in co-pending U.S. Appl. No. 13/610,954.
Notice of allowance dated Aug. 30, 2017 in co-pending U.S. Appl. No. 13/610,954.
Chinese communication, with English translation, dated Oct. 30, 2017 in co-pending Chinese patent application No. 201510375479.1.
Office action dated Oct. 25, 2017 in co-pending U.S. Appl. No. 13/732,613.
Final rejection dated Mar. 20, 2018 in co-pending U.S. Appl. No. 13/732,613.
Zeppezauer et al., "Protein Precipitation by Uncharged Water-Soluble Polymers", Biochimica et Biophysica Acta, vol. 94, Mar. 29, 1965, pp. 581-583.
Advisory action dated Jun. 19, 2017 in co-pending U.S. Appl. No. 13/732,613.
Indian communication, with English translation, dated Oct. 17, 2018 in co-pending Indian patent application No. 4539/DELNP/2011.

* cited by examiner though the column to be discarded. The protein then is
recovered by elution from the column. Since most of the
proteins of interest have isoelectric points (PI) in the basic
range (8-9) and therefore being positively charged under
normal processing conditions (pH below the PI of the
protein), they are bound to the cation exchange resin in the
second column. Other positively charged impurities are also
bound to this resin. The protein of interest is then recovered
by elution from this column under conditions (pH, salt
concentration) in which the protein elutes while the impurities remain bound to the resin. The anion exchange column
PURIFICATION OF PROTEINS

CROSS-REFERENCED TO RELATED APPLICATIONS

This application is a Divisional of U.S. patent application Ser. No. 12/316,708, filed on Dec. 16, 2008, which is a Continuation-in-Part application of U.S. application Ser. No. 12/004,319, filed on Dec. 20, 2007 (now U.S. Pat. No. 8,362,217, issued on Jan. 29, 2013), which claims the benefit of priority of U.S. Provisional Patent Application No. 60/876,330, filed on Dec. 21, 2006, the entire contents of which are incorporated by reference herein.

The present invention relates to the purification of biomolecules. More particularly, it relates to the purification of biomolecules such as proteins, polypeptides, antibodies and the like, by a stimuli responsive polymer, such as a solubilized or soluble polymer to capture the desired biomolecules from a solution/suspension by a precipitation mechanism and then to further purify it.

BACKGROUND OF THE INVENTION

The general process for the manufacture of biomolecules, such as proteins, particularly recombinant proteins typically involves two main steps: (1) the expression of the protein in a host cell, followed by (2) the purification of the protein. The first step involves growing the desired host cell in a bioreactor to effect the expression of the protein. Some examples of cell lines used for this purpose include Chinese hamster ovary (CHO) cells, myeloma (NSO) bacterial cells such as e-coli and insect cells. Once the protein is expressed at the desired levels, the protein is removed from the host cell and harvested. Suspended particulates, such as cells, cell fragments, lipids and other insoluble matter are typically removed from the protein-containing fluid by filtration or centrifugation, resulting in a clarified fluid containing the protein of interest in solution as well as other soluble impurities.

The second step involves the purification of the harvested protein to remove impurities which are inherent to the process. Examples of impurities include host cell proteins (HCP, proteins other than the desired or targeted protein), nucleic acids, endotoxins, viruses, protein variants and protein aggregates.

This purification typically involves several chromatography steps, which can include affinity, ion exchange hydrophobic interaction, etc on solid matrices such as porous agarose, polymeric or glass or by membrane based adsorbers.

One example of a chromatography process train for the purification of proteins involves use of protein-A affinity for the purification of monoclonal antibodies, followed by cation exchange, followed by anion exchange. The protein-A column captures the protein of interest or target protein by an affinity mechanism while the bulk of the impurities pass is typically operated in a flow through mode, such that any negatively charged impurities are bound to the resin while the positively charged protein of interest is recovered in the flow through stream. This process results in a highly purified and concentrated protein solution.

Other alternative methods for purifying proteins have been investigated in recent years, one such method involves a flocculation technique. In this technique, a soluble polyelectrolyte is added to an unclarified cell culture broth to capture the suspended particulates and a portion of the soluble impurities thereby forming a flocculent, which is subsequently removed from the protein solution by filtration or centrifugation.

Alternatively, a soluble polyelectrolyte is added to clarified cell culture broth to capture the biomolecules of interest, thereby forming a flocculent, which is allowed to settle and can be subsequently isolated from the rest of the solution. The flocculent is typically washed to remove loosely adhering impurities. Afterwards, an increase in the solution's ionic strength brings about the dissociation of the target protein from the polyelectrolyte, subsequently resulting in the resolubilization of the polyelectrolyte into the protein-containing solution.

The main drawback of this flocculation technique is that it requires that the polyelectrolyte be added in the exact amount needed to remove the impurities or capture the biomolecule of interest. If too little flocculent is added, impurities and/or a portion of the target biomolecule (protein, peptide, polypeptide, antibody fragment, etc) will remain in the solution. On the other hand, if too much flocculent is added, the excess polyelectrolyte needs to be removed from the resulting solution. The exact level of impurities in the broth is extremely difficult to predict due to the relatively large degree of variability in the process (from batch to batch) as well as the vast differences between processes to produce different proteins. Removing any excess polyelectrolyte is practically impossible because it is a soluble material and thus it is carried through the process as an undesirable impurity.

In co-pending application U.S. Ser. No. 12/004,314 filed Dec. 20, 2007, a polymer, soluble under certain conditions, such as temperature, pH, salt, light or combinations thereof, is used to bind impurities while in its soluble state and is then precipitated out upon a change in condition (pH or temperature, etc) removing the impurities with it. The biomolecule of interest is then further treated using traditional chromatography or membrane adsorbers and the like.

In co-pending application U.S. Ser. No. 12/004,319 filed Dec. 20, 2007 it was suggested that one would use the clarification process and chemistries of the application mentioned above to provide one with a clarified feedstock and then use the different chemistries and processes of this case to purify the biomolecule of interest.

All of the protein purification technologies discussed above share a common theme, and said theme is to first remove suspended particulates in a first distinct step and then in a second step separate the biomolecules of interest from soluble impurities which are inherent to the process.

In situ product recovery with derivatized magnetic particles is one example of a protein purification technique where the biomolecules of interest can be purified directly from an un-clarified cell culture broth. In this technique, a polymer shell encapsulating a magnetic bead is functionalized with an affinity ligand that seeks out and binds the target protein. A magnetic field is then applied to collect the bead-protein complexes, leaving behind the soluble impurities and insoluble particulates.

The main drawback of this technique is that it requires appreciable capital investments in design, construction and validation of high-gradient magnetic separators. Also, the technique does not lend itself to disposable applications, which are poised to become the norm for protein purification in the Bioprocess industry.

What is needed is a better process for purifying biomolecules in fewer steps with fewer materials.

SUMMARY OF THE INVENTION

The present invention relates to a polymer such as a soluble polymer capable of irreversibly binding to insoluble particulates and a subset of soluble impurities and also capable of reversibly binding to one or more desired biomolecules in an unclarified biological material containing stream and the methods of using such a material to purify one or more desired biomolecules from such a stream without the need for prior clarification.

The present invention relates to a stimuli responsive polymer such as a selectively soluble polymer capable of selectively and reversibly binding to one or more desired biomolecules in an unclarified biological material containing stream and the methods of using such a polymer to purify one or more desired biomolecules from such a complex mixture of materials including the biomolecule(s) of interest and various impurities such as other proteins (host cell proteins), DNA, virus, whole cells, cellular debris and the like without the need for prior clarification of the stream.

The polymer is soluble under a certain set of process conditions such as one or more of pH, salt concentration, temperature, light, or electrical field, and is able to interact and complex with insoluble impurities (cells, debris, etc.) and a fraction of the soluble impurities, and is rendered insoluble and precipitates out of solution upon a change in conditions (temperature, salt concentration, light, electrical field, or pH), e.g. a stimuli responsive polymer. Only when precipitated out of solution, the polymer is capable of reversibly binding to one or more desired biomolecules within the stream (protein, polypeptide, etc) in an unclarified cell broth. The precipitate can then be removed from the stream, such as by being filtered out from the remainder of the stream and the desired biomolecule is recovered such as by selective elution from the precipitate. The stream is then discarded removing with it the great majority of the impurities of the mixture such as cell culture media, anti foam materials, additives, and soluble components.

The precipitate that contains the polymer, impurities such as cells and cell debris, host cell proteins, DNA and the like and the desired biomolecule, can be washed one or more times to ensure that any impurities in the liquid remaining in the precipitate or entrapped in or on the polymer have been removed. The biomolecule of interest can then be recovered, such as by selective elution of the target biomolecule from the precipitate by altering the ionic strength and/or pH conditions of the solution while the impurities, including soluble and insoluble material, remain complexed with the precipitated polymer. The purified target biomolecule is recovered in the elution pool and the precipitated polymer-impurity complex is discarded.

It is an object of the present invention to provide a stimuli responsive polymer to be soluble in a given condition and to become insoluble and form a precipitate in response to a change in condition.

It is an object of the present invention to provide a polymer that is capable of being selectively solubilized in a liquid under certain conditions and to be insoluble and to precipitate out of solution under different conditions in that liquid.

It is another object of the present invention to provide a polymer that is capable of being selectively solubilized in a liquid under certain conditions and to be insoluble and to precipitate out of solution under different conditions in that liquid and to allow for an overage of the polymer in solution and being able to recover substantially all the polymer from solution by precipitation.

It is a further object of the present invention to provide a polymer that is capable of being solubilized under a first certain set of conditions in the liquid and to be capable of binding to one or more entities in the liquid after being precipitated from the liquid under different conditions.

It is another object of the present invention to provide a polymer capable of being solubilized under certain ranges of pH, temperature, salt, temperature and salt concentration or the like and to have it bind to one or more desired biomolecules either during or after being precipitated under a different set of ranges of pH, temperature, salt, temperature and salt concentration or the like.

It is an object to use one or more polymers such as poly(N-vinyl caprolactam), poly(N-acryloylpiperidine), poly(N-vinylisobutyramide), poly (N-substituted acrylamide) including [poly(N-isopropylacrylamide), poly(N,N'-diethylacrylamide), and poly(N-acryloyl-N'-alkylpiperazine)], Hydroxyalkylcellulose, copolymers of acrylic acid and methacrylic acid, polymers and copolymers of 2 or 4-vinylpyridine and chitosan with either a ligand or functional group attached to it to selectively capture and reversibly bind to a desired biomolecule in order to purify the biomolecule from a stream containing the biomolecule along with one or more impurities or other entities.

It is a further object of the present invention to provide a process for purifying a selected biomolecule from a biomolecule containing stream by either having the stream at a given condition or modifying the stream to a given condition and adding a polymer soluble in the stream at that given condition, allowing the solubilized polymer to circulate throughout the stream, changing the given condition of the stream so as to cause the polymer to become insoluble in the stream and bind the desired biomolecule, separating the stream from the polymer and processing the polymer further to recover the desired biomolecule by elution while maintaining the polymer in its precipitated (solid) form.

It is an object to do the process with an overabundance of polymer and recover all the polymer as a precipitate from the mixture.

It is an additional object of the present invention to provide the process based on a polymer which is soluble based upon a condition selected from temperature, salt, temperature and salt content or pH.

It is another object of the present invention to provide a polymer selected from homopolymers of 2 or 4-vinylpyridine, polymers containing 2 or 4-vinylpyridine, with one or more monomers, such as copolymers of 2 or 4-vinylpyridine with styrene, copolymers of 2 or 4-vinylpyridine with methyl methacrylate, copolymers of 2 or 4-vinylpyridine with butyl methacrylate, copolymers of 2 or 4-vinylpyridine with N-isopropylacrylamide, poly(2 or 4-vinylpyridine) grafted hydroxyalkylcellulose, and poly(methacrylic acid-co-methylmethacrylate).

It is a further object of the present invention to provide a polymer selected from homopolymers of 2 or 4-vinylpyridine, polymers containing 2 or 4-vinylpyridine, with one or more monomers, such as copolymers of 2 or 4-vinylpyridine with styrene, copolymers of 2 or 4-vinylpyridine with methyl methacrylate, copolymers of 2 or 4-vinylpyridine with butyl methacrylate, copolymers of 2 or 4-vinylpyridine with N-isopropylacrylamide, poly(2 or 4-vinylpyridine) grafted hydroxyalkylcellulose, and poly(methacrylic acid-co-methylmethacrylate) and wherein the polymer either has a functional group, such as a carboxyl or pyridine or substituted pyridine group, attached to the polymer that binds to the biomolecule of interest.

It is a further object of the present invention to provide a process for purifying a selected biomolecule from a biomolecule containing mixture by setting the mixture to a given condition, modifying a carrier liquid compatible with the mixture to the same given condition, adding a polymer soluble in the carrier liquid at that given condition to the carrier liquid and allowing the polymer to dissolve in the carrier which can be a solvent or dispersant for the polymer, adding the carrier liquid with the solubilized or dispersed polymer to the mixture and allowing it to circulate throughout the mixture, changing the given condition of the stream so as to cause the polymer to become insoluble in the stream, bind the desired biomolecule as well as much of the impurities, in particular the cells or cellular debris and precipitate out along with the one or more biomolecules and other components the mixture, separating the mixture from the polymer and recovering the entity.

It is an additional object of the present invention to provide a static mixer for causing the mixture and solubilized polymer to mix and to allow the polymer to bind to the one or more biomolecules after being precipitated under a different set of ranges of pH, temperature, salt, temperature and salt concentration or the like.

It is another object of the present invention to provide that the one or more entities are a biomolecule in the mixture.

It is a further embodiment of the present invention to provide a purified biomolecule in an elution solution such as a buffer solution that is compatible with the next downstream process in order to reduce or eliminate buffer exchanges between the various processing steps.

It is an additional object of the present invention to provide a process for the purification of a mixture of biological constituents in a single step.

It is a further object of the present invention to provide a process for the purification of a mixture of biological constituents including desired biomolecules and impurities and recovering the biomolecules in a single step.

It is another object of the present invention to provide a process for the purification of a mixture of biological constituents selected from proteins, polypeptides, monoclonal antibodies, humanized, chimeral or animal monoclonal antibodies polyclonal antibodies, antibody fragments, multispecific antibodies, immunoadhesins, and $C_H2/C_H3$ region-containing proteins.

It is a further object of the present invention to provide a process of having a mixture containing a biomolecule of interest at a set range of conditions that will cause one or more polymers of choice to go into solution, adding the one or more polymers and having one or more polymers go into solution, mixing the one or more soluble polymers with entities of the mixture changing the conditions of the mixture to cause the one or more polymers to precipitate out of solution while pulling both the biomolecule(s) of interest and some impurities out of the mixture as part of the precipitate, separating the precipitate from the remainder of the mixture and recovering the biomolecule(s) of interest from the precipitate.

It is a further object of the present invention to provide a process of having a mixture containing a biomolecule of interest at a set range of conditions that will cause one or more polymers of choice to go into solution, adding the one or more polymers and having one or more polymers go into solution, mixing the one or more soluble polymers with the mixture, changing the conditions of the mixture to cause the one or more polymers to precipitate out of solution pulling the biomolecule(s) of interest and some impurities out with the precipitate, separating the precipitate from the remainder of the mixture, while retaining one or more biomolecule(s) to the precipitate. The precipitate is kept as a solid while the biomolecule(s) is eluted off the precipitated polymer and impurities. and the biomolecule(s) is recovered such as by filtration, decantation or centrifugation for further processing.

It is a further object of the present invention to provide a process of having a mixture containing a biomolecule of interest at a set range of conditions that will cause one or more polymers of choice to go into solution, adding the one or more polymers and having one or more polymers go into solution, mixing the one or more insoluble polymers with entities of the mixture changing the conditions of the mixture to cause the one or more polymers to precipitate out of solution and then separating the precipitate from the remainder of the mixture, while retaining one or more biomolecule(s) and some impurities of the mixture bound to the precipitate. The biomolecule(s) is then eluted from the precipitate under conditions that keep the polymer in its precipitated form without attaching to the biomolecule(s) and the biomolecule(s) is recovered such as by filtration, decantation or centrifugation for further use or processing.

It is a further object of the present invention to provide a carrier liquid for the polymer having conditions suitable to cause the polymer to go into solution in the carrier liquid and then to add the carrier liquid with the dissolved polymer to the mixture.

It is an additional object of the present invention to provide one or more static mixers to mix the polymer and the mixture.

It is a further object of the present invention to provide a process for recovering a biomolecule of interest from an unclarified mixture obtained from a fermentor or bioreactor in which it has been made.

It is an additional object of the present invention to provide a filtration step to separate the precipitate from the remainder of the mixture.

It is another object of the present invention to provide a normal flow filtration step to separate the precipitate from the remainder of the mixture.

It is a further object of the present invention to provide a tangential flow filtration step to separate the precipitate from the remainder of the mixture.

It is an additional object of the present invention to provide a centrifugation step to separate the precipitate from the remainder of the mixture.

It is another object of the present invention to provide a decantation step to separate the precipitate from the remainder of the mixture.

It is an additional object of the present invention to provide a further step to recover the one or more constituents of the mixture from the precipitated polymer by elution under conditions that keep the polymer in its precipitated form.

It is a further object of the present invention to provide additional processing to the biomolecule of interest.

It is an additional object of the present invention to provide a further step of formulating the biomolecule in a pharmaceutically acceptable carrier and using it for various diagnostic, therapeutic or other uses known for such biomolecules.

It is an object of the present invention to provide a purified biomolecule in one step, directly in or out of the bioreactor.

It is a further object of the present invention to use a UF step to concentrate the biomolecule after it has been purified and recovered with the precipitation technique.

It is an additional object of the present invention to effect the purification and recovery of a biomolecule with additional processing using an enhanced UF (charged UF) process.

DETAILED DESCRIPTION OF THE INVENTION

Figure 1:
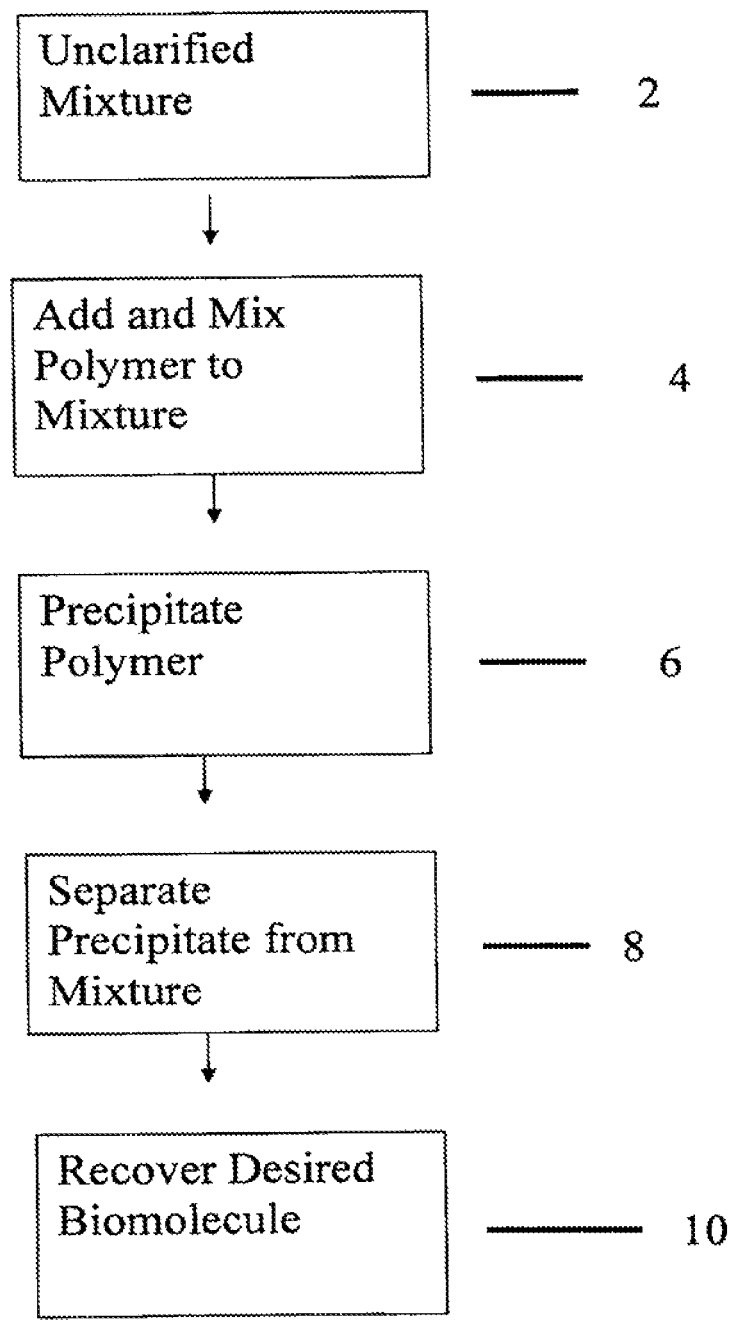
FIG. 1 shows a block diagram of a first process according to the present invention.

The invention is to use a liquid phase or solubilized polymer that has a capability even when precipitated, such as affinity or charge or hydrophobicity and the like, to selectively and reversibly bind to at least one or more biomolecules of interest and optionally one or more impurities in an unclarified liquid. . . . The biomolecule of interest is then selectively eluted from the polymer preferably while the polymer is preferably retained in its solid or precipitated form with any impurities still attached to it. The biomolecule is then recovered for further processing.

More specifically, the idea relates to the process of using one or more polymers soluble in a liquid phase to selectively bind to one or more desired biomolecules in a solution/suspension by a precipitation mechanism and which polymer can also be removed, if present, in any excess, by the same mechanism. By way of example, this idea can best be described in the context of protein purification although it can be used to purify any solute molecule from complex mixtures as long as the mechanism of removal applies to the specific solute of interest.

The one or more polymers can be used in excess unlike flocculants and can be recovered essentially completely from the mixture by the precipitation action. This allows one to operate the purification step with greater windows of use and without having to calculate the precise amount of material that needs to be used.

The present concept is based on the fact that certain polymers undergo changes in properties as a result of changes in the environment (stimuli) in which they are in, i.e. stimuli responsive polymers. The most common polymer property to change as a result of a stimulus is solubility and the most common stimuli relating to solubility are temperature, light, electric field, salt concentration, pH and combinations of them such as salt concentration and pH. As an example, a polymer may remain in solution as long as the pH, salt level, light, electrical field or temperature is maintained within a certain range but it will precipitate out of solution as soon as the condition is changed outside of said range. Certain polymers, such as poly(N-vinyl caprolactam), poly(N-acryloylpiperidine), poly(N-vinylisobutyramide), poly (N-substituted acrylamide) including [poly(N-isopropylacrylamide), poly(N,N'-diethylacrylamide), and poly(N-acryloyl-N'-alkylpiperazine)] and hydroxyalkylcellulose are examples of polymers that exhibit solubility changes as a result of changes in temperature. Other polymers, such as copolymers of acrylic acid and methacrylic acid, polymers and copolymers of 2 or 4-vinylpyridine and chitosan exhibit changes in solubility as a result of changes in pH or salt.

As some of these polymers may not have an ability to selectively bind or elute the desired molecules of interest and/or impurities, they need to be modified with ligands or chemical groups that will complex with the desired molecule and hold it in complex and then release the desired molecule under the appropriate elution conditions. What happens if we don't remove the cells? Suitable chemical groups can include but are not limited to carboxyl groups and pyridine groups formed as part of the polymer or attached to the polymer. Ligands such as chemical mimics of affinity ligands may be used. Such ligands include but are not limited to natural ligands or synthetic ligands such as mercaptoethylpyridine (MEP), mercaptoethylpyrazine, MEB, 2-aminobenzimidazole (ABI), AMBI, 2-mercaptobenzoic acid (MBA), 4-amino-benzoic acid (ABA), 2-mercapto-benzimidazole (MBI) and the like.

Depending upon the polymer used, the process used can vary.

Preferred temperature sensitive soluble polymers include but are not limited to functional copolymers of N-isopropylacrylamide, functionalized agarose and functionalized polyethylene oxide.

Preferred pH sensitive soluble polymers include but are not limited to cationic polyelectrolytes and anionic polyelectrolytes. Preferred cationic polyelectrolytes are selected from the group consisting of chitosan, polyvinylpyridines, primary amine containing polymers, secondary amine containing polymers and tertiary amine containing polymers. Preferred anionic polyelectrolytes selected from the group consisting of copolymers of acrylic acid, methacrylic acid and methyl methacrylate.

Unlike in the prior inventions, one can use unclarified cell culture fluid containing the biomolecule of interest along with cell culture media components as well as cell culture additives, such as anti-foam compounds and other nutrients and supplements, cells, cellular debris, host cell proteins, DNA, viruses and the like in the present invention. Moreover, the process can be conducted, if desired, in the bioreactor itself.

The fluid may either be preconditioned to a desired stimulus such as pH, temperature or other stimulus characteristic or the fluid can be conditioned upon addition of the polymer(s) or the polymer(s) can be added to a carrier liquid that is properly conditioned to the required parameter for the stimulus condition required for that polymer to be solubilized in the fluid. The polymer(s) is allowed to circulate thoroughly with the fluid and then the stimulus is applied (change in pH, temperature, salt concentration, etc) and the desired biomolecule and polymer(s) precipitate out of solution. The polymer and desired biomolecule(s) is separated from the rest of the fluid and optionally washed one or more times to remove any trapped or loosely bound contaminants. The desired biomolecule is then recovered from the polymer(s) such as by elution and the like. Preferably, the elution is done under a set of conditions such that the polymer remains in its solid (precipitated) form and retains any impurities to it during the selective elution of the desired biomolecule. Alternatively, the polymer and biomolecule as well as any impurities can be solubilized in a new fluid such as water or a buffered solution and the biomolecule be recovered by a means such as affinity, ion exchange, hydrophobic, or some other type of chromatography that has a preference and selectivity for the biomolecule over that of the polymer or impurities. The eluted biomolecule is then recovered and if desired subjected to additional processing steps, either traditional batch like steps or continuous flow through steps if appropriate.

The soluble polymer(s) such as poly(N-vinyl caprolactam), poly(N-acryloylpiperidine), poly(N-vinylisobutyramide), poly (N-substituted acrylamide) including [poly(N-isopropylacrylamide), poly(N,N'-diethylacrylamide), and poly(N-acryloyl-N'-alkylpiperazine)],hydroxyalkylcellulose, copolymers of acrylic acid and methacrylic acid or methacrylic acid and methyl methacrylate, polymers and copolymers of 2 or 4-vinylpyridine and chitosan may contain a functional group and/or ligand that binds to the biomolecule of interest or it may act by hydrophobic action or other such well known chromatographic type actions with the biomolecule.

The processes will generally involve having one or more conditions of the liquid of the mixture, at the correct pH, temperature, light, electrical field or salt concentration or other condition used to cause the polymer(s) to become soluble and then adding the polymer(s) either directly or already solubilized in a carrier liquid, such as water or buffered solution, to the mixture. In some instances, the mixture will be at the proper condition to allow the polymer(s) to be simply added to the mixture.

In other instances, the mixture may need to be conditioned or modified to be at the desired condition. This modification or conditioning can be by modifying the mixture first and then adding the polymer(s), by adding the polymer(s) to a carrier liquid that is conditioned to the desired state and simply adding it to the mixture such that the carrier liquid is sufficient to cause the mixture to thus reach that condition or to do both.

The conditions of the liquid in the mixture are then changed (pH, temperature, salt content, combinations thereof, etc) that causes the polymer(s) to become insoluble and precipitate out of the mixture as a dispersed solid suspension. The mixture and the suspended insoluble polymer(s) are then mixed to ensure that the biomolecules of interest in the mixture and the insolubilized polymer(s) have sufficient and intimate contact with each other and some of the impurities of the mixture. In most instances the impurities are the insoluble materials such as whole cells or cellular debris. Most if not all soluble impurities are removed with the liquid of the mixture when it is separated from the precipitant. In some instances, the insoluble polymer(s) bind the one or more desired biomolecules it contacts while in the mixture and continues to bind to it thereafter until elution conditions are met to remove the biomolecule from the polymer. In others the polymer(s) bind to one or more impurities such as cells or cellular debris and entrain the biomolecule along with the impurities during its shift to a precipitate. Lastly, in some embodiments both the biomolecule and impurities are simply entrained out of the mixture by the precipitation of the polymer(s).

The precipitate is separated such as by centrifugation or filtration or gravity and time with the liquid portion being decanted. The recovered polymer is optionally washed one or more times to remove any loosely bound residual impurities or contaminants and then the biomolecule(s) is eluted from the polymer under conditions that cause the biomolecule entity to release from the polymer so it can be recovered and subjected to further processing or use. Preferably, the elution conditions are such that the polymer remains in its solid or precipitated form and the eluted biomolecule is separated from the polymer by simple filtration, using a filter that allows the biomolecule through but retains the solid polymer upstream.

One polymer or a blend of polymers may be used in the present invention and it is meant to cover both embodiments whenever the term polymer, polymer(s) or one or more polymers is used hereafter.

As discussed above, the polymer may be added directly to the mixture either as is or in a conditioned state that allows the polymer to be solubilized as it is added. Alternatively, it can be added to a carrier liquid in which it is soluble or dispersable and which carrier preferably is also compatible with the mixture. One such carrier liquid is water, water adjusted to a specific pH using acid or base, another is an aqueous based solution such as saline, physiological buffers or blends of water with an organic solvent such as water/alcohol blends. The selection of carrier liquid is dependent on the mixture to which it is added as to what is preferred and tolerated. The polymer is added to the carrier liquid that either has already been conditioned (such as pH adjusted or heated to a desired temperature or heated to a desired temperature with the addition of one or more salts or cooled to the desired temperature with or without one or more salts) or it can be added and then the carrier is conditioned to cause the solubilizing of the polymer in the carrier. The carrier/soluble polymer blend is then added to the mixture.

The mixture may be contained in a mixing vessel such as a tapered bottom metal (preferably stainless steel more preferably 304 or 316L stainless steel) or glass or plastic bag, vat or tank. Alternatively, especially when a cell culture or microbial or yeast culture, it may be the bioreactor or fermentor in which the cells have been grown. It may also be a disposable bioreactor or fermentor or a disposable mixing bag such as a plastic bag as is available from Millipore Corporation of Billerica, Mass. The mixture and polymer are brought into intimate contact through a mixing action that may be done by a magnetic stirred bar, a magnetic driven mixer such as a NovAseptic® or a Mobius® mixer available from Millipore Corporation of Billerica, Mass., a Lightning-type mixer, a recirculation pump, or a rocking motion closed mixing bag or bioreactor or fermentor, such as is shown in US 2005/0063259A1 or U.S. Pat. No. 7,377,686 or an airlift type of mixer or reactor in which rising bubbles in the liquid cause a circulatory pattern to be formed.

Alternatively, the mixture and polymer (either by itself or in a carrier) can be in separate containers and mixed in line in a static blender. The blend can either then go to a container or to a centrifuge or a filter where the precipitated polymer and its bound one or more biomolecule entities is separated from the remainder of the mixture and then is further processed.

In another embodiment, the mixture and polymer (either by itself or in a carrier) are blended together in the container holding the mixture and further mixed in line in a static blender. The blend can either then go to a container or to a centrifuge or to a filter where the precipitated polymer and its bound one or more biomolecule entities and cells or other impurities are separated from the remainder of the mixture. Then the precipitated polymer is further processed to recover the biomolecule of interest.

Using centrifugation, one can easily and quickly separate the precipitated polymer from the remainder of the liquid mixture. After centrifugation, the supernatant, generally the remainder of the mixture is drawn off. The precipitated polymer is further processed.

If desired, the supernatant may be subjected to one or more additional polymer precipitation steps to recover even more of the desired biomolecule.

Simple decantation may also be used if desired.

The use of settling due to density differences may also be used and the separated materials deanted or otherwise separated from each other after that.

Filtration can be accomplished in a variety of manners. Depending upon the size of the polymer as it is precipitated; one may use one or more filters of varying sizes or asymmetries. The selection of type and size of filter will depend on the volume of precipitate to be captured.

Membrane based filters, preferably microporous membranes can be used in the present invention. Such filters are generally polymeric in nature and can be made from polymers such as but not limited to olefins such as polyethylene including ultrahigh molecular weight polyethylene, polypropylene, EVA copolymers and alpha olefins, metallocene olefinic polymers, PFA, MFA, PTFE, polycarbonates, vinyl copolymers such as PVC, polyamides such as nylon, polyesters, cellulose, cellulose acetate, regenerated cellulose, cellulose composites, polysulfone, polyethersulfone, polyarylsulfone, polyphenylsulfone, polyacrylonitrile, polyvinylidene fluoride (PVDF), and blends thereof. The membrane selected depends upon the application, desired filtration characteristics, particle type and size to be filtered and the flow desired. Preferred membrane based filters include DURAPORE® PVDF membranes available from Millipore Corporation of Billerica Mass., MILLIPORE EXPRESS® and MILLIPORE EXPRESS® PLUS or SH PES membranes available from Millipore Corporation of Billerica Mass. Prefilters, depth filters and the like can also be used in these embodiments such as Polygard® prefilters (Polygard CE prefilters) and depth filters (Polygard CR depth filters) available from Millipore Corporation of Billerica Mass.

Depending on the mixture, polymer and the nature of biomolecule, the filter, such a membrane, may be hydrophilic or hydrophobic. Preferred membranes are hydrophilic and are low in protein binding.

The membrane may be symmetric in pore size through out its depth such as DURAPORE® PVDF membranes available from Millipore Corporation of Billerica Mass., or it may be asymmetric in pore size through its thickness as with MILLIPORE EXPRESS® and MILLIPORE EXPRESS® PLUS or SH PES membranes available from Millipore Corporation of Billerica Mass. It may contain a prefilter layer if desired, either as a separate upstream layer or as an integral upstream portion of the membrane itself.

The filter or prefilter or depth filter may be formed of non-membrane materials such as continuous wound fiber, fibrous mats (Millistak+® pads) and/or non woven materials such as Tyvek® plastic paper.

The pore size of the membrane can vary depending upon the polymer and mixture selected. Generally, it has an average pore size of from about 0.05 micron to 5 microns, preferably from about 0.05 micron to about 1 micron, more preferably from about 0.05 to about 0.65 micron.

Prefilters and depth filters often are not rated by pore size but to the extent that they are they may have a pore size of from about 0.22 micron to about 10 micron.

The filter be it membrane, non woven, pad or other form may run in a deadend or normal flow (NF) format or a tangential flow (TFF) format. The choice is dependent on a number of factors, primarily the user's preference or installed filtration equipment as either works with the present invention. A TFF process and equipment is preferred when large amounts of polymer and molecule are to be recovered as TFF is less subject to clogging or fouling than NF methods.

FIG. 1 shows a block diagram of a first process of the present invention. In the first step 2, the unclarified mixture is either conditioned to the correct parameter(s) so as to maintain the capture polymer of choice in solution when added or if the conditions of the mixture are already such that the polymer(s) become soluble in the mixture, no further conditioning may be required. Alternatively, the polymer(s) may be added as a solid to an unconditioned mixture and then the mixture (containing the solid polymer(s)) may be conditioned to the correct parameters to dissolve the polymer(s) in the mixture. Likewise, the polymer can be added to a carrier liquid and added at the correct conditions to the mixture. The mixture itself may also be preconditioned or it may rely on the carrier to condition it upon its introduction. In the second step 4, the polymer(s) is mixed with the mixture in the stream for desirable amount of time to create suitable distribution to make intimate contact with all the constituents of the mixture. In the third step 6, the conditions of the liquid in the mixture are then changed (pH, temperature, salt content, combinations thereof, etc) to cause the polymer(s) to become insoluble and precipitate out of the mixture as a dispersed solid suspension while retaining the biomolecule and cells or other impurities. The rest of the mixture and the precipitated polymer(s) are then separated from each other in the fourth step 8. As discussed above the precipitate and remaining mixture may be separated by centrifugation, decantation or filtration.

The precipitate can then optionally be washed one or more times with water (not shown), a buffer or an intermediate wash solution as are known in the art to remove any impurities from the precipitate or any non-specifically bound impurities from the precipitate.

The desired biomolecule is then recovered. Preferably it is eluted from the polymer such as by the addition of a buffer at a pH (acidic or basic depending on the molecule and the polymer used) and/or the salt concentration or temperature of the solution is changed to allow for the recovery of the desired molecule free of the polymer in step 10. Preferably the elution conditions are such that the polymer remains in its solid (precipitated) form although it can if desired or needed be rendered soluble again.

Figure 2:
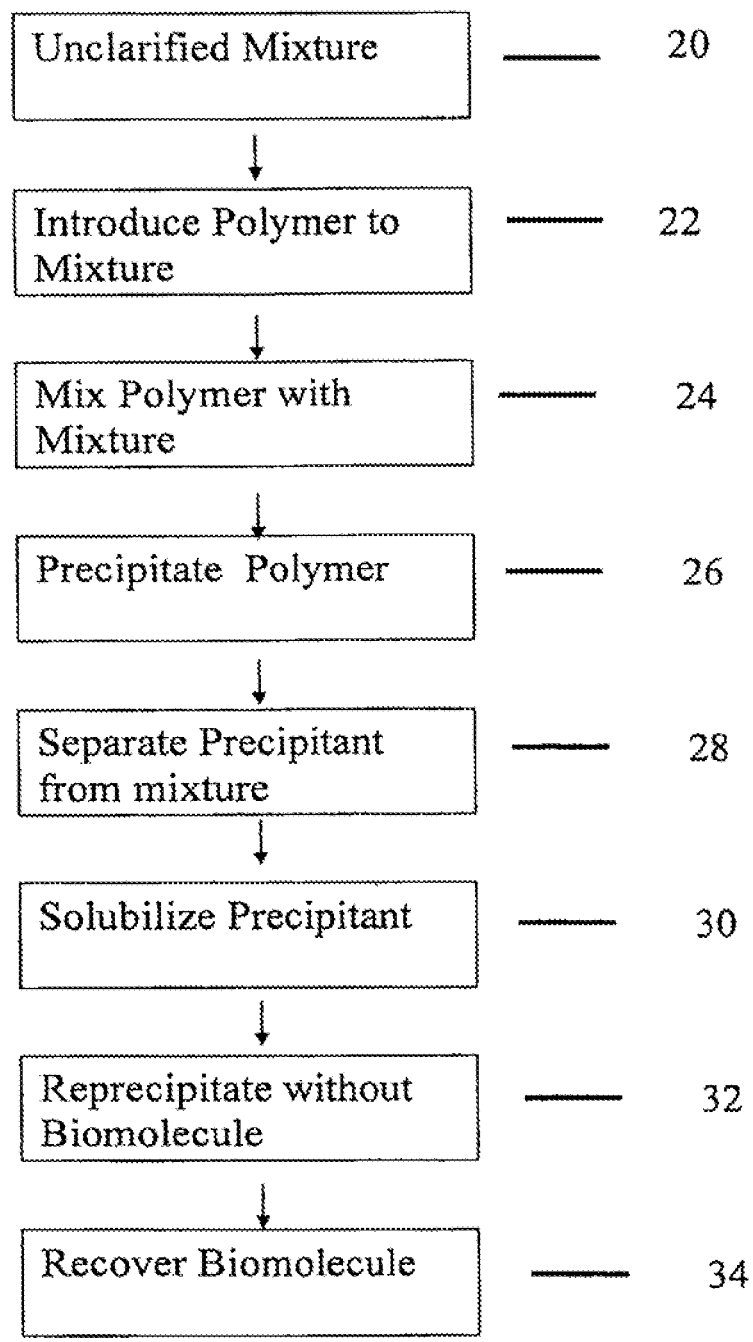
FIG. 2 shows a block diagram of a second process according to the present invention.

FIG. 2 shows a block diagram of this process as applied to a pH dependent polymer such as poly(4-vinylpyridine-co-styrene), (10% mol styrene) which has an affinity, be it chemical, electrical, phobic/philic, etc for the desired biomolecule in the insoluble state. In the first step 20, the mixture is either conditioned to the correct pH (in this case to a pH below about 5.0) to maintain the polymer of choice in solution before, during or after the introduction of the polymer or it is already at the desired condition in a second step 22. In the third step 24 which may occur separately before, simultaneously or after the second step 22, the polymer is added to a carrier liquid under conditions that allow it to go into solution and then mixed to make intimate contact with all the constituents of the mixture so that the polymer can complex with the desired molecule (for example a IgG molecule, cells, etc.

In the fourth step 26, the mixture conditions are changed to cause the polymer to precipitate out of solution in the form of a dispersed solid suspension.

If desired one may conduct one or more additional steps to ensure that all polymer has been removed from the mixture by subjecting the mixture to a step containing a material that will remove any residual polymer from the mixture such as ion exchange resin, activated carbon, alumina, diatomaceous earth and the like. Typically however the polymer is removed on the first precipitation and such additional steps are not necessary.

As discussed above, the precipitate and remaining mixture may be separated by centrifugation, decantation or filtration in a fifth step 28. Optionally, the polymer and complex are washed one or more times while being kept under conditions such that the polymer/biomolecule(s)/cells precipitate remains undissociated.

To recover the molecule, the conditions are changed, such as by lowering the pH or changing the ionic strength of the solution, so as to break the complex between the polymer and the biomolecule in the sixth step 30. The elution liquid is removed from the precipitated polymer by filtration, decantation or centrifugation or the like and the eluted biomolecule is recovered in the seventh step 32. Optionally, (and not shown in FIG. 2) one can solubilize the polymer and then change the conditions of the liquid such that the bond between the biomolecule and polymer is broken (such as pH or ionic change), then change the conditions again such that the polymer and impurities are reprecipitated and the biomolecule remains in solution. The biomolecule is then recovered by filtration, decantation, centrifugation and the like.

The biomolecule of interest after having been recovered, may undergo one or more known additional process steps such as chromatography steps including but not limited to ion exchange, hydrophobic interaction or affinity chromatography, various filtration steps such as microfiltration, ultrafiltration, high performance tangential flow filtration (HPTFF) with or without charged UF membranes, viral removal/inactivation steps, final filtration steps and the like. Alternatively, the eluted biomolecule of interest may be used as is without the need for further purification steps. Also the biomolecule of interest may undergo further purification without the need for chromatography steps.

In a further embodiment, it eliminates at least the step of clarification and preferably the steps of clarification and affinity chromatography. A biological process under this embodiment would consist of capture of the biomolecule directly from the unclarified mixture via the polymer-based purification step, separation of the biomolecule from the polymer and the remainder of the mixture, two or more steps of viral removal or inactivation such as removal through viral filters or inactivation through treatment with heat, chemicals or light, a compounding step into the correct formulation and a final filtering before filling the compounded biomolecule into its final container for use (vial, syringe, etc).

In any of the embodiments of the present invention the biomolecule such as a protein thus recovered may be formulated in a pharmaceutically acceptable carrier and is used for various diagnostic, therapeutic or other uses known for such molecules.

The mixture that is the starting material of the process will vary depending upon the cell line in which it was grown as well as the conditions under which it is grown and harvested. For example, in most CHO cell processes the cells express the molecule outside of the cell wall into the media. One tries not to rupture the cells during harvest in order to reduce the amount of impurities in the mixture. However, some cells during growth and harvesting may rupture due to shear or other handling conditions or die and lyse, spilling their contents into the mixture. In bacteria cell systems, the biomolecule is often kept with the cellular wall or it may actually be part of the cellular wall (Protein A). In these systems, the cell walls need to be disrupted or lysed in order to recover the biomolecule of interest.

The target molecule to be purified can be any biomolecule, preferably a protein, in particular, recombinant protein produced in any host cell, including but not limited to, Chinese hamster ovary (CHO) cells, Per.C6® cell lines available from Crucell of the Netherlands, myeloma cells such as NSO cells, other animal cells such as mouse cells, insect cells, or microbial cells such as *E. coli* or yeast. Additionally, the mixture may be a fluid derived from an animal modified to produce a transgenic fluid such as milk or blood that contains the biomolecule of interest. Optimal target proteins are antibodies, immunoadhesins and other antibody-like molecules, such as fusion proteins including a $C_H2/C_H3$ region. In particular, this product and process can be used for purification of recombinant humanized monoclonal antibodies such as (RhuMAb) from a conditioned harvested cell culture fluid (HCCF) grown in Chinese hamster ovary (CHO) cells expressing RhuMAb.

Antibodies within the scope of the present invention include, but are not limited to: anti-HER2 antibodies including Trastuzumab (HERCEPTIN®) (Carter et al., *Proc. Natl. Acad. Sci. USA*, 89:4285-4289 (1992), U.S. Pat. No. 5,725,856); anti-CD20 antibodies such as chimeric anti-CD20 "C2B8" as in U.S. Pat. No. 5,736,137 (RITUXAN.®), a chimeric or humanized variant of the 2H7 antibody as in U.S. Pat. No. 5,721,108, B1, or Tositumomab (BEXXAR.®); anti-IL-8 (St John et al., *Chest*, 103:932 (1993), and International Publication No. WO 95/23865); anti-VEGF antibodies including humanized and/or affinity matured anti-VEGF antibodies such as the humanized anti-VEGF antibody huA4.6.1 AVASTIN®. (Kim et al., *Growth Factors*, 7:53-64 (1992), International Publication No. WO 96/30046, and WO 98/45331, published Oct. 15, 1998); anti-PSCA antibodies (WO01/40309); anti-CD40 antibodies, including S2C6 and humanized variants thereof (WO00/75348); anti-CD11a (U.S. Pat. No. 5,622,700, WO 98/23761, Steppe et al., *Transplant Intl.* 4:3-7 (1991), and Hourmant et al., *Transplantation* 58:377-380 (1994)); anti-IgE (Presta et al., *J Immunol.* 151:2623-2632 (1993), and International Publication No. WO 95/19181); anti-CD18 (U.S. Pat. No. 5,622,700, issued Apr. 22, 1997, or as in WO 97/26912, published Jul. 31, 1997); anti-IgE (including E25, E26 and E27; U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338); anti-Apo-2 receptor antibody (WO 98/51793 published Nov. 19, 1998); anti-TNF-α antibodies including cA2 (REMICADE®), CDP571 and MAK-195 (See, U.S. Pat. No. 5,672,347 issued Sep. 30, 1997, Lorenz et al. *J. Immunol.* 156(4):1646-1653 (1996), and Dhainaut et al. *Crit. Care Med.* 23(9):1461-1469 (1995)); anti-Tissue Factor (TF) (European Patent No. 0 420 937 B1 granted Nov. 9, 1994); anti-human $\alpha_4\beta_7$ integrin (WO 98/06248 published Feb. 19, 1998); anti-EGFR (chimerized or humanized 225 antibody as in WO 96/40210 published Dec. 19, 1996); anti-CD3 antibodies such as OKT3 (U.S. Pat. No. 4,515,893 issued May 7, 1985); anti-CD25 or anti-tac antibodies such as CHI-621 (SIMULECT®) and (ZENAPAX®) (See U.S. Pat. No. 5,693,762 issued Dec. 2, 1997); anti-CD4 antibodies such as the cM-7412 antibody (Choy et al. *Arthritis Rheum* 39(1):52-56 (1996)); anti-CD52 antibodies such as CAMPATH-1 H (Riechmann et al. *Nature* 332:323-337 (1988)); anti-Fc receptor antibodies such as the M22 antibody directed against FcγRI as in Graziano et al. *J. Immunol.* 155(10):4996-5002 (1995); anti-carcinoembryonic antigen (CEA) antibodies such as hMN-14 (Sharkey et al. *Cancer Res.* 55(23Suppl): 5935s-5945s (1995); antibodies directed against breast epithelial cells including huBrE-3, hu-Mc 3 and CHL6 (Ceriani et al. *Cancer Res.* 55(23): 5852s-5856s (1995); and Richman et al. *Cancer Res.* 55(23 Supp): 5916s-5920s (1995)); antibodies that bind to colon carcinoma cells such as C242 (Litton et al. *Eur J. Immunol.* 26(1):1-9 (1996)); anti-CD38 antibodies, e.g. AT 13/5 (Ellis et al. *J. Immunol.* 155(2):925-937 (1995)); anti-CD33 antibodies such as Hu M195 (Jurcic et al. *Cancer Res* 55(23 Suppl):5908s-5910s (1995) and CMA-676 or CDP771; anti-CD22 antibodies such as LL2 or LymphoCide (Juweid et al. *Cancer Res* 55(23 Suppl):5899s-5907s (1995)); anti-EpCAM antibodies such as 17-1A (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®; anti-HIV antibodies such as PRO542; anti-hepatitis antibodies such as the anti-Hep B antibody OSTAVIR®; anti-CA 125 antibody OvaRex; anti-idiotypic GD3 epitope antibody BEC2; anti-$\alpha v \beta_3$ antibody VITAXIN®.; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1). The preferred target antigens for the antibody herein are: HER2 receptor, VEGF, IgE, CD20, CD11a, and CD40.

Aside from the antibodies specifically identified above, the skilled practitioner could generate antibodies directed against an antigen of interest, e.g., using the techniques described below.

The antibody herein is directed against an antigen of interest. Preferably, the antigen is a biologically important polypeptide and administration of the antibody to a mammal suffering from a disease or disorder can result in a therapeutic benefit in that mammal. However, antibodies directed against non-polypeptide antigens (such as tumor-associated glycolipid antigens; see U.S. Pat. No. 5,091,178) are also contemplated. Where the antigen is a polypeptide, it may be a transmembrane molecule (e.g. receptor) or ligand such as a growth factor. Exemplary antigens include those proteins described in section (3) below. Exemplary molecular targets for antibodies encompassed by the present invention include CD proteins such as CD3, CD4, CD8, CD19, CD20, CD22, CD34, CD40; members of the ErbB receptor family such as the EGF receptor, HER2, HER3 or HER4 receptor; cell adhesion molecules such as LFA-1, Mad, p150, 95, VLA-4, ICAM-1, VCAM and αv/β3 integrin including either α or β subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; protein C, or any of the other antigens mentioned herein. Antigens to which the antibodies listed above bind are specifically included within the scope herein.

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule.

Other antigens and forms thereof useful for preparing antibodies will be apparent to those in the art.

Polyclonal antibodies can also be purified in the present invention. Polyclonal antibodies are preferably raised in animals by multiple subcutaneous (sc) or intraperitoneal (ip) injections of the relevant antigen and an adjuvant. It may be useful to conjugate the antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N\!=\!C\!=\!NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to 1/10 the original amount of antigen or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies are of interest in the present invention and may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, Pro-Sep® Protein A media available from Millipore Corporation of Billerica, Mass., hydroxyapatite chromatography, gel electrophoresis, dialysis, or affinity chromatography. Preferably the Protein A chromatography procedure described herein is used.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells.

The DNA also may be modified, for example, by substituting the coding sequence for human heavy- and light-chain constant domains in place of the homologous murine sequences (U.S. Pat. No. 4,816,567; Morrison, et al., *Proc. Natl. Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In a further embodiment, monoclonal antibodies can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional hybridoma techniques for isolation of monoclonal antibodies.

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human FR for the humanized antibody (Sims et al., *J. Immunol.*, 151:2296 (1993)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and Duchosal et al. *Nature* 355:258 (1992). Human antibodies can also be derived from phage-display libraries (Hoogenboom et al., *J. Mol. Biol.*, 227:381 (1991); Marks et al., *J. Mol. Biol.*, 222:581-597 (1991); Vaughan et al. *Nature Biotech* 14:309 (1996)).

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

Multispecific antibodies have binding specificities for at least two different antigens. While such molecules normally will only bind two antigens (i.e. bispecific antibodies, BsAbs), antibodies with additional specificities such as trispecific antibodies are encompassed by this expression when used herein.

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells over expressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994). Alternatively, the antibodies can be "linear antibodies" as described in Zapata et al. *Protein Eng.* 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

Antibodies with more than two valencies are contemplated. For example, trispecific antibodies can be prepared. Tutt et al. *J. Immunol.* 147: 60 (1991).

The simplest and most straightforward immunoadhesin design combines the binding domain(s) of the adhesin (e.g. the extracellular domain (ECD) of a receptor) with the hinge and Fc regions of an immunoglobulin heavy chain. Ordinarily, when preparing the immunoadhesins of the present invention, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, $C_H2$ and $C_H3$ domains of the constant region of an immunoglobulin heavy chain. Fusions are also made to the C-terminus of the Fc portion of a constant domain, or immediately N-terminal to the $C_H1$ of the heavy chain or the corresponding region of the light chain. The precise site at which the fusion is made is not critical; particular sites are well known and may be selected in order to optimize the biological activity, secretion, or binding characteristics of the immunoadhesin.

In a preferred embodiment, the adhesin sequence is fused to the N-terminus of the Fc domain of immunoglobulin $G_1$ ($IgG_1$). It is possible to fuse the entire heavy chain constant region to the adhesin sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the adhesin amino acid sequence is fused to (a) the hinge region and $C_H2$ and $C_H3$ or (b) the $C_H1$, hinge, $C_H2$ and $C_H3$ domains, of an IgG heavy chain.

For bispecific immunoadhesins, the immunoadhesins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Various exemplary assembled immunoadhesins within the scope herein are schematically diagrammed below:

(a) $AC_L$-$AC_L$;
(b) $AC_H$-($AC_H$, $AC_L$-$AC_H$, $AC_L$-$V_HC_H$, or $V_LC_L$-$AC_H$);
(c) $AC_L$-$AC_H$-($AC_L$-$AC_H$, $AC_L$-$V_HC_H$, $V_LC_L$-$AC_H$, or $V_LC_L$-$V_HC_H$)
(d) $AC_L$-$V_HC_H$-($AC_H$, or $AC_L$-$V_HC_H$, or $V_LC_L$-$AC_H$);
(e) $V_LC_L$-$AC_H$-($AC_L$-$V_HC_H$, or $V_LC_L$-$AC_H$); and
(f) $(A-Y)_n$-$(V_LC_L$-$V_HC_H)_{23}$ wherein each A represents identical or different adhesin amino acid sequences;

$V_L$ is an immunoglobulin light chain variable domain;
$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed to be present in the ordinary locations which they occupy in the immunoglobulin molecules.

Alternatively, the adhesin sequences can be inserted between immunoglobulin heavy chain and light chain sequences, such that an immunoglobulin comprising a chimeric heavy chain is obtained. In this embodiment, the adhesin sequences are fused to the 3' end of an immunoglobulin heavy chain in each arm of an immunoglobulin, either between the hinge and the $C_H2$ domain, or between the $C_H2$ and $C_H3$ domains. Similar constructs have been reported by Hoogenboom, et al., Mol. Immunol. 28:1027-1037 (1991).

Although the presence of an immunoglobulin light chain is not required in the immunoadhesins of the present invention, an immunoglobulin light chain might be present either covalently associated to an adhesin-immunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued 28 Mar. 1989.

Immunoadhesins are most conveniently constructed by fusing the cDNA sequence encoding the adhesin portion in-frame to an immunoglobulin cDNA sequence. However, fusion to genomic immunoglobulin fragments can also be used (see, e.g. Aruffo et al., Cell 61:1303-1313 (1990); and Stamenkovic et al., Cell 66:1133-1144 (1991)). The latter type of fusion requires the presence of 1 g regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the immunoglobulin parts of the immunoadhesin are inserted in tandem into a plasmid vector that directs efficient expression in the chosen host cells.

In other embodiments, the protein to be purified is one which is fused to, or conjugated with, a $C_H2/C_H3$ region. Such fusion proteins may be produced so as to increase the serum half-life of the protein. Examples of biologically important proteins which can be conjugated this way include renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-p; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD3, CD4, CD8, CD19, CD20, CD34, and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

The following examples are offered by way of illustration and not by way of limitation. The disclosures of all citations in the specification are expressly incorporated herein by reference.

EXAMPLES

Example 1 ph Adjustment of an Unclarified Cell Culture Fluid

Cells derived from a non-expressing Chinese Hampster Ovary (CHO) cell line were grown in a bioreactor (New Brunswick Scientific) to a density of $2\times10^6$ cells/ml in 10 L of culture medium and harvested at 64% viability. IgG was spiked to a concentration of 0.8 g/L and the concentrations of host cell proteins (HCP) was 4075 ng/ml. The pH of the fluid was 7.2. The pH of the unclarified cell culture fluid was adjusted to 4.5 using 0.5 ml of 1.0M HCl, prior to the start of the purification process.

Example 2

This Example Illustrates the Removal of Residual 4-vinyl Pyridine Monomer from Poly(4-vinylpyridine)

Linear poly(4-vinylpyridine), (PVP) MW 200,000 obtained form Scientific Polymer Products, Inc., was spread evenly on a glass dish and placed in a vacuum oven. The atmosphere inside the oven was purged with argon for 5 minutes several times to remove oxygen. The pressure in the oven was reduced to 0.1 in mercury using a mechanical vacuum pump and subsequently the temperature was raised to 120° C. The polymer was subjected to these conditions for a total of 24 hours. During this time, the atmosphere inside the oven was purged with argon for 5 minutes several times. At the end of the heating period, the oven temperature was lowered to room temperature and the oven was purged with argon several times before opening the door. The resulting polymer did not have a noticeable odor, whereas the untreated polymer has a distinct odor of 4-vinyl pyridine monomer. The amount of residual 4-vinyl pyridine monomer present in the treated polymer was not detectable by gel permeation chromatography whereas the untreated polymer had 0.05% (w/w) residual 4-vinyl pyridine monomer

Example 3

This Example Illustrates the Removal of Residual 4-vinyl Pyridine and Styrene Monomers from Poly(4-vinylpyridine-co-styrene)

Linear poly(4-vinylpyridine-co-styrene), (PVP-co-PS), 10% styrene content, obtained form Scientific Polymer Products, Inc., was treated exactly according to the process of example 2. The resulting polymer did not have a noticeable odor, whereas the untreated polymer has a distinct odor of 4-vinyl pyridine and styrene monomers.

Example 4

This Example Illustrates the Preparation of a PVP-co-PS Solution

A 10% (w/w) solution of PVP-co-PS was prepared by dissolving 10 g purified PVP-co-PS, from example 3, in 90 g 1.0 M hydrochloric acid with continuous agitation for 16 hours at room temperature. The resulting viscous solution was slightly hazy.

Example 5

This Example Illustrates the Capture and Subsequent Elution of IgG from Un-clarified Cell Culture Fluid Using PVP-co-PS 1.0 g of the PVP-co-PS solution from example 4 was added to 25 ml of the pH-adjusted un-clarified cell culture fluid from example 1 and mixed at room temperature for 5 minutes, to allow for binding of insoluble impurities, such as cells and cell debris as well as soluble impurities, such as host cell proteins, nucleic acids, etc. To the resulting solution, 0.75 g sodium perchlorate in 1.6 ml sodium hydroxide (0.4 M) was added to precipitate the polymer-impurities complex and to effect the binding of IgG to the complex. The precipitate, in the form of a dispersed solid suspension was mixed continuously in the fluid for 10 min. The precipitate-IgG complex was then collected by centrifugation (4000 rpm for 1 min) and washed with phosphate buffer (50 mM, 0.2M sodium perchlorate, pH 4.5) to remove loosely-bound impurities. While cells, cell debris and other soluble impurities remained bound to the precipitate, selective elution of the IgG from the precipitate took place at pH 3.6 (10 mM sodium acetate, 0.1M NaCl) followed by filtration through 0.2μ Durapore® filters. Under these conditions, 95% of the IgG present in the original fluid was bound to the polymer and the IgG recovered upon elution was 75 wt %.

Example 6

This Example Illustrates the Capture and Subsequent Elution of IgG from Un-clarified Cell Culture Fluid Using PVP-co-PS 1.0 g of the PVP-co-PS solution from example 4 and 3.3 g ammonium sulfate were added to 25 ml of the pH-adjusted un-clarified cell culture fluid from example 1 and mixed at room temperature for 5 minutes to allow for binding of insoluble impurities, such as cells and cell debris as well as soluble impurities, such as host cell proteins, nucleic acids, etc. The polymer-impurities complex was then precipitated by adjusting the pH of the mixture to 8.5 using sodium hydroxide (1.0 N), this allows the IgG to bind to the complex. The precipitate, in the form of a dispersed solid suspension was mixed continuously in the fluid for 10 min. The precipitate-IgG complex was then collected by centrifugation (4000 rpm for 1 min) and washed with phosphate buffer (50 mM, 1.0 M ammonium sulfate, pH 8.5) to remove loosely-bound impurities. Re-solubilization of the precipitate and elution of the IgG took place at pH 4.0 in acetate buffer (10 mM and 0.1 M lithium chloride). Removal of the resolubilized polymer-cells complex was effected by adding 0.3M sodium trifluoromethane sulfonate, which caused the polymer-cells complex to precipitate out of solution, followed by filtration through 0.2μ Durapore® filters. Under these conditions, 95% of the IgG present in the original fluid was bound to the polymer and the IgG recovered upon elution was 87 wt %.

Example 7

This Example Illustrates the Capture and Subsequent Elution of IgG from an Un-clarified Cell Culture Fluid Using PVP-co-PS 1.0 g of the PVP-co-PS solution from example 4 and 3.3 g ammonium sulfate were added to 25 ml of the pH-adjusted un-clarified cell culture fluid from example 1 and mixed at room temperature for 5 minutes to allow for binding of insoluble impurities, such as cells and cell debris as well as soluble impurities, such as host cell proteins, nucleic acids, etc. The polymer-impurities complex was then precipitated by adjusting the pH of the mixture to 8.5, this allows the IgG to bind to the complex. The precipitate, in the form of a dispersed solid suspension was mixed continuously in the fluid for 10 min. The precipitate-IgG complex was then collected by centrifugation (4000 rpm for 1 min) and washed with phosphate buffer (50 mM, 1.0 M ammonium sulfate, pH 8.5) to remove loosely-bound impurities. While cells, cell debris and other soluble impurities remained bound to the precipitate-selective elution of the IgG from the precipitate took place at pH 3.5 (10 mM sodium acetate, 0.1M lithium chloride, 20 mM sodium perchlorate) followed by filtration through 0.2μ Durapore® filters. Under these conditions, 95% of the IgG present in the original fluid was bound to the polymer and the IgG recovered upon elution was 75 wt %.

Example 8

This Example Illustrates the Level of Host Cell Protein (HCP) in a Solution Containing a Desired Biomolecule (IgG) that was Captured Using PVP-co-PS The experiment was carried out as illustrated in Example 5. An ELISA assay kit (Cygnus CM015, lot17077) was used to track the level of host cell protein (HCP) at different steps of the product (IgG) capture process.

The concentration of HCP was reduced from 4075 ng/ml in the starting cell culture fluid to 176 ng/ml in the elution sample (96% reduction).

Example 9

This Example Illustrates the Level of HCP in a Solution Containing a Desired Biomolecule (IgG) that was Captured Using PVP-co-PS The experiment was carried out as illustrated in Example 6. An ELISA assay kit (Cygnus CM015, lot17077) was used to track the level of host cell protein (HCP) at different steps of the product (IgG) capture process.

The concentration of HCP was reduced from 4075 ng/ml in the starting cell culture fluid to 300 ng/ml in the elution sample (93% reduction).

Example 10

This Example Illustrates the Level of HCP in a Solution Containing a Desired Biomolecule (IgG) that was Captured Using PVP-co-PS The experiment was carried out as illustrated in Example 7. An ELISA assay kit (Cygnus CM015, lot17077) was used to track the level of host cell protein (HCP) at different steps of the product (IgG) capture process.

The concentration of HCP was reduced from 4075 ng/ml in the starting cell culture fluid to 290 ng/ml in the elution sample (93% reduction).

Example 11

This Example Illustrates the Level of DNA in a Solution Containing a Desired Biomolecule (IgG) that was Captured Using PVP-co-PS The experiment was carried out as illustrated in Example 5. The quantification of DNA in the different steps of the IgG capture process was carried out by Pico-Green assay. The levels of DNA in the starting cell culture fluid and elution samples were 44 μg/ml and 0.063 μg/ml respectively.

Example 12

This Example Illustrates the Level of Minute Mouse Virus (MMV) in a Solution Containing a Desired Biomolecule (IgG) that was Captured Using PVP-co-PS Unclarified cell culture fluid was spiked with $1 \times 10^6$ $TCID_{50}$/ml and the IgG purification process was carried out as described in Example 5. The concentration of MMV virus in the elution sample was decreased by 3.6 Logs.

Example 13

This Example Illustrates the Level of Xenotropic Murine Leukemia Virus (X-MuLv) in a Solution Containing a Desired Biomolecule (IgG) that was Captured Using PVP-co-PS Unclarified cell culture fluid were spiked with $1 \times 10^5$ $TCID_{50}$/ml and the IgG purification process was carried out as described in Example 5. No virus was detected in the elution sample. Under these conditions, the minimum detectable 10 g reduction value (LRV) was 3.

Example 14

This Example Illustrates the Synthesis of poly(4-vinyl pyridine-co-vinylimidazole), PVP-co-VI 4-vinyl pyridine, 1-vinylimidazole, Dimethylformamide, methanol and toluene were obtained from Sigma. 2,2-Azobis(2-amidinopropane) hydrochloride was obtained form Scientific polymer products, Inc. 4-vinyl pyridine was purified using an inhibitor removal column (Sigma); all other chemicals were used as received.

A solution of 12.45 g (0.118 mole) of 4-vinyl pyridine, 2.78 g (0.03 mole) of 1-vinylimidazole, and 0.09 g (0.25 mol %) of the initiator 2,2-Azobis(2-amidinopropane) hydrochloride in 10 ml of Water-DMF solution (50:50 Vol %) was maintained at T=85° C. for 48 hr under an argon atmosphere. After cooling to room temperature, the resulting solid was dissolved in 50 ml methanol and precipitated in toluene. The precipitate was further washed with 30 ml diethylether, and then dried in an oven at 70° C. for 24 hr with a yield of 75%. The mole ratio of the reactants was selected such that the product comprises 20 mol % of vinylimidazole.

Example 15

This Example Illustrates the Preparation of a PVP-co-VI solution

A 10% (w/w) solution of PVP-co-VI was prepared by dissolving 10 g purified PVP-co-VI, from example 14, in 90 g 1.0 M hydrochloric acid with continuous agitation for 1 hour at room temperature. The resulting viscous solution was clear and slightly yellow in color Example 16

Production of an Unclarified Cell Culture Fluid Containing IgG at a Concentration of 5.0 g/L Cells derived from a non-expressing Chinese Hampster Ovary (CHO) cell line were grown in a bioreactor (New Brunswick Scientific) to a density of $2\times10^6$ cells/ml in 10 L of culture medium and harvested at 64% viability. IgG was spiked to a concentration of 5.0 g/L and the concentrations of host cell proteins (HCP) was 4075 ng/ml. The pH of the fluid was 7.2.

Example 17

This Example Illustrates the Capture of IgG from Un-clarified Cell Culture Fluid Using PVP-co-VI Sodium perchlorate monohydrate, hydrochloric acid (1.0 M) and Sodium hydroxide (1.0 M) were obtained from Fisher Scientific.

2.5 g of the polymer solution from example 15 were added to 20 ml of un-clarified cell culture fluid from example 16 and mixed at room temperature for 10 minutes to allow for binding of insoluble impurities, such as cells and cell debris as well as soluble impurities, such as host cell proteins, nucleic acids, etc. The polymer-impurities complex, was then precipitated by adding 0.56 g sodium perchlorate in 1.3 ml sodium hydroxide (1.0 M), this allows the IgG to bind to the complex. The precipitate, in the form of a dispersed solid suspension was mixed continuously in the fluid for 10 min the desired product (IgG). The precipitate-product complex was then collected by centrifugation (4000 rpm for 1 min) and the supernatant was filtered through 0.2μ Durapore® filters. Under these conditions, 99% of the IgG present in the original fluid was bound to the polymer.

Example 18

This Example Illustrates the Preparation of a PVP Solution

A 10% (w/w) solution of PVP was prepared by dissolving 10 g purified PVP, from example 2, in 90 g 1.0 M hydrochloric acid with continuous agitation for 16 hours at room temperature. The resulting viscous solution was clear and had a slight yellow color.

Example 19

This Example Illustrates the Capture of IgG from Un-clarified Cell Culture Fluid Using poly(4-vinyl pyridine), PVP Sodium perchlorate monohydrate, hydrochloric acid (1.0 M) and Sodium hydroxide (1.0 M) were from Fisher Scientific.

2.5 g of the polymer solution from example 18 were added to 20 ml of un-clarified cell culture fluid from example 16 and mixed at room temperature for 10 minutes to allow for binding of insoluble impurities, such as cells and cell debris as well as soluble impurities, such as host cell proteins, nucleic acids, etc. The polymer-impurities complex, was then precipitated by adding 0.56 g sodium perchlorate in 1.3 ml sodium hydroxide (1.0 M), this allows the product (IgG) to bind to the complex. The precipitate, in the form of a dispersed solid suspension was mixed continuously in the fluid for 10 min. The precipitate-product complex was then collected by centrifugation (4000 rpm for 1 min) and the supernatant was filtered through 0.2μ Durapore® filters. Under these conditions, 99% of the IgG present in the original fluid was bound to the polymer.

Example 20

Production of an Unclarified Cell Culture Fluid Containing IgG at a Concentration of 10.0 g/L Cells derived from a non-expressing Chinese Hampster Ovary (CHO) cell line were grown in a bioreactor (New Brunswick Scientific) to a density of $2\times10^6$ cells/ml in 10 L of culture medium and harvested at 64% viability. IgG was spiked to a concentration of 10.0 g/L and the concentrations of host cell proteins (HCP) was 4075 ng/ml. The pH of the fluid was 7.2.

Example 21

This Example Illustrates the Capture of IgG from Un-clarified Cell Culture Fluid Using PVP-co-VI Sodium perchlorate monohydrate, hydrochloric acid (1.0 M) and Sodium hydroxide (1.0 M) were obtained from Fisher Scientific.

5.0 g of the polymer solution from example 15 were added to 20 ml of un-clarified cell culture fluid from example 20 and mixed at room temperature for 10 minutes to allow for binding of insoluble impurities, such as cells and cell debris as well as soluble impurities, such as host cell proteins, nucleic acids, etc. The polymer-impurities complex, was then precipitated by adding 0.56 g sodium perchlorate in 2.6 ml sodium hydroxide (1.0 M), this allows the product (IgG) to bind to the complex. The precipitate, in the form of a dispersed solid suspension was mixed continuously in the fluid for 10 min. The precipitate-product complex was then collected by centrifugation (4000 rpm for 1 min) and the supernatant was filtered through 0.2μ Durapore® filters. Under these conditions, 99% of the IgG present in the original fluid was bound to the polymer.

Example 22

This Example Illustrates the Capture of IgG from Un-clarified Cell Culture Fluid Using poly(4-vinyl pyridine), PVP Sodium perchlorate monohydrate, hydrochloric acid (1.0 M) and Sodium hydroxide (1.0 M) were from Fisher Scientific.

5.0 g of the polymer solution from example 18 were added to 20 ml of un-clarified cell culture fluid from example 20 and mixed at room temperature for 10 minutes to allow for binding of insoluble impurities, such as cells and cell debris as well as soluble impurities, such as host cell proteins, nucleic acids, etc. The polymer-impurities complex, was then precipitated by adding 0.56 g sodium perchlorate in 2.6 ml sodium hydroxide (1.0 M), this allows the desired product (IgG) to bind to the complex. The precipitate, in the form of a dispersed solid suspension was mixed continuously in the fluid for 10 min. The precipitate-product complex was then collected by centrifugation (4000 rpm for 1 min) and the supernatant was filtered through 0.2µ Durapore® filters. Under these conditions, 99% of the IgG present in the original fluid was bound to the polymer.

Example 23

This Example Illustrates the Capture of IgG from Un-clarified Cell Culture Fluid Using poly(4-vinyl pyridine), PVP 0.3 g of the PVP solution from example 18 and 1.32 g ammonium sulfate were added to 10 ml of the pH-adjusted un-clarified cell culture fluid from example 1 and mixed at room temperature for 5 minutes to allow for binding of insoluble impurities, such as cells and cell debris as well as soluble impurities, such as host cell proteins, nucleic acids, etc. The polymer-impurities complex, was then precipitated by adjusting the pH of the mixture to 8.5, this allows the desired product (IgG) to bind to the complex. The precipitate, in the form of a dispersed solid suspension was mixed continuously in the fluid for 10 min. The precipitate-IgG complex was then collected by centrifugation (4000 rpm for 1 min) and washed with phosphate buffer (50 mM, 1.0 M ammonium sulfate, pH 8.5) to remove loosely-bound impurities. While cells, cell debris and other soluble impurities remained bound to the precipitate-selective elution of the IgG from the precipitate took place at pH 3.5 (25 mM citric acid), while mixing for 20 mins, followed by filtration through 0.2µ Durapore® filters. Under these conditions, 93% of the IgG present in the original fluid was bound to the polymer and the IgG recovered upon elution was 90 wt %.

Example 24

This Example Illustrates the Capture of IgG from Un-clarified Cell Culture Fluid Using poly(4-vinyl pyridine), PVP 0.3 g of the PVP solution from example 18 and 1.32 g ammonium sulfate were added to 10 ml of the pH-adjusted un-clarified cell culture fluid from example 1 and mixed at room temperature for 5 minutes to allow for binding of insoluble impurities, such as cells and cell debris as well as soluble impurities, such as host cell proteins, nucleic acids, etc. The polymer-impurities complex, was then precipitated by adjusting the pH of the mixture to 8.5, this allows the desired product (IgG) to bind to the complex. The precipitate, in the form of a dispersed solid suspension was mixed continuously in the fluid for 10 min. The precipitate-IgG complex was then collected by centrifugation (4000 rpm for 1 min) and washed with phosphate buffer (50 mM, 1.0 M ammonium sulfate, pH 8.5) to remove loosely-bound impurities. While cells, cell debris and other soluble impurities remained bound to the precipitate-selective elution of the IgG from the precipitate took place at pH 3.5 (50 mM sodium hydrogen tartrate), while mixing for 20 mins, followed by filtration through 0.2µ Durapore® filters. Under these conditions, 95% of the IgG present in the original fluid was bound to the polymer and the IgG recovered upon elution was 85 wt %.

Example 25

This Example Illustrates the Capture of IgG from Un-clarified Cell Culture Fluid Using poly(4-vinyl pyridine), PVP 0.3 g of the PVP solution from example 18 and 1.32 g ammonium sulfate were added to 10 ml of the pH-adjusted un-clarified cell culture fluid from example 1 and mixed at room temperature for 5 minutes to allow for binding of insoluble impurities, such as cells and cell debris as well as soluble impurities, such as host cell proteins, nucleic acids, etc. The polymer-impurities complex, was then precipitated by adjusting the pH of the mixture to 8.5, this allows the desired product (IgG) to bind to the complex. The precipitate, in the form of a dispersed solid suspension was mixed continuously in the fluid for 10 min. The precipitate-IgG complex was then collected by centrifugation (4000 rpm for 1 min) and washed with phosphate buffer (50 mM, 1.0 M ammonium sulfate, pH 8.5) to remove loosely-bound impurities. While cells, cell debris and other soluble impurities remained bound to the precipitate-selective elution of the IgG from the precipitate took place at pH 3.2 (100 mM citric acid), while mixing for 20 mins, followed by filtration through 0.2µ Durapore® filters. Under these conditions, 90% of the IgG present in the original fluid was bound to the polymer and the IgG recovered upon elution was 88 wt %.

Example 26

This Example Illustrates the Capture of IgG from Un-clarified Cell Culture Fluid Using poly(4-vinyl pyridine), PVP 2.5 g of the PVP solution from example 18 and 2.64 g ammonium sulfate were added to 20 ml of un-clarified cell culture fluid from example 16 and mixed at room temperature for 5 minutes to allow for binding of insoluble impurities, such as cells and cell debris as well as soluble impurities, such as host cell proteins, nucleic acids, etc. The polymer-impurities complex, was then precipitated by adjusting the pH of the mixture to 8.5, this allows the desired product (IgG) to bind to the complex. The precipitate, in the form of a dispersed solid suspension was mixed continuously in the fluid for 10 min. The precipitate-IgG complex was then collected by centrifugation (4000 rpm for 1 min) and washed with phosphate buffer (50 mM, 1.0 M ammonium sulfate, pH 8.5) to remove loosely-bound impurities. While cells, cell debris and other soluble impurities remained bound to the precipitate, selective elution of the IgG from the precipitate took place at pH 3.5 (100 mM citric acid), while mixing for 20 mins, followed by filtration through 0.2μ Durapore® filters. Under these conditions, 99% of the IgG present in the original fluid was bound to the polymer and the IgG recovered upon elution was 88 wt %.

Example 27

This Example Illustrates the Capture of IgG from Un-clarified Cell Culture Fluid Using poly(4-vinyl pyridine), PVP 5.0 g of the PVP solution from example 18 and 2.64 g ammonium sulfate were added to 20 ml of un-clarified cell culture fluid from example 20 and mixed at room temperature for 5 minutes to allow for binding of insoluble impurities, such as cells and cell debris as well as soluble impurities, such as host cell proteins, nucleic acids, etc. The polymer-impurities complex, was then precipitated by adjusting the pH of the mixture to 8.5, this allows the desired product (IgG) to bind to the complex. The precipitate, in the form of a dispersed solid suspension was mixed continuously in the fluid for 10 min. The precipitate-IgG complex was then collected by centrifugation (4000 rpm for 1 min) and washed with phosphate buffer (50 mM, 1.0 M ammonium sulfate, pH 8.5) to remove loosely-bound impurities. While cells, cell debris and other soluble impurities remained bound to the precipitate, selective elution of the IgG from the precipitate took place at pH 3.5 (100 mM citric acid), while mixing for 20 mins, followed by filtration through 0.2μ Durapore® filters. Under these conditions, 99% of the IgG present in the original fluid was bound to the polymer and the IgG recovered upon elution was 89 wt %.

Example 28

This Example Illustrates the Selective Binding of Intact IgG Versus a Population of IgG Fragments from an Un-clarified Cell Culture Fluid Using poly(4-vinyl pyridine), PVP Supernatant and elution samples from examples 23 & 25 were analyzed by sodium dodecyl sulfate polyacrylamide gel electrophoresis (SDS-PAGE) according to the method of Laemmli (UK Laemmli (1970) Cleavage of structural proteins during the assembly of the head of bacteriophage T4. Nature 227, 680-685). Each sample was diluted two-fold in Laemmli sample buffer (Bio-Rad 161-0737). Laemmli buffer was used directly for analysis under non-reducing conditions. Each sample was incubated for 10 minutes at 100 C before loading onto the gels. Separations were accomplished using 4-15% gradient gels with 10 wells (Bio-Rad 161-1104) or 15 wells (Bio-Rad 161-1122) and Tris-Glycine-SDS running buffer (ThermoFisher BP1341). Molecular weight markers were included on each gel (Bio-Rad 161-0374). Gels were run at constant voltage, using 200 V for 35 minutes. Following the separation, proteins were visualized using Gel Code Blue (ThermoFisher 24591) according to the manufacturer's protocol. The cell culture fluid from example 1 was used as a control and the data appear in the table and figure below.

Figure 3:
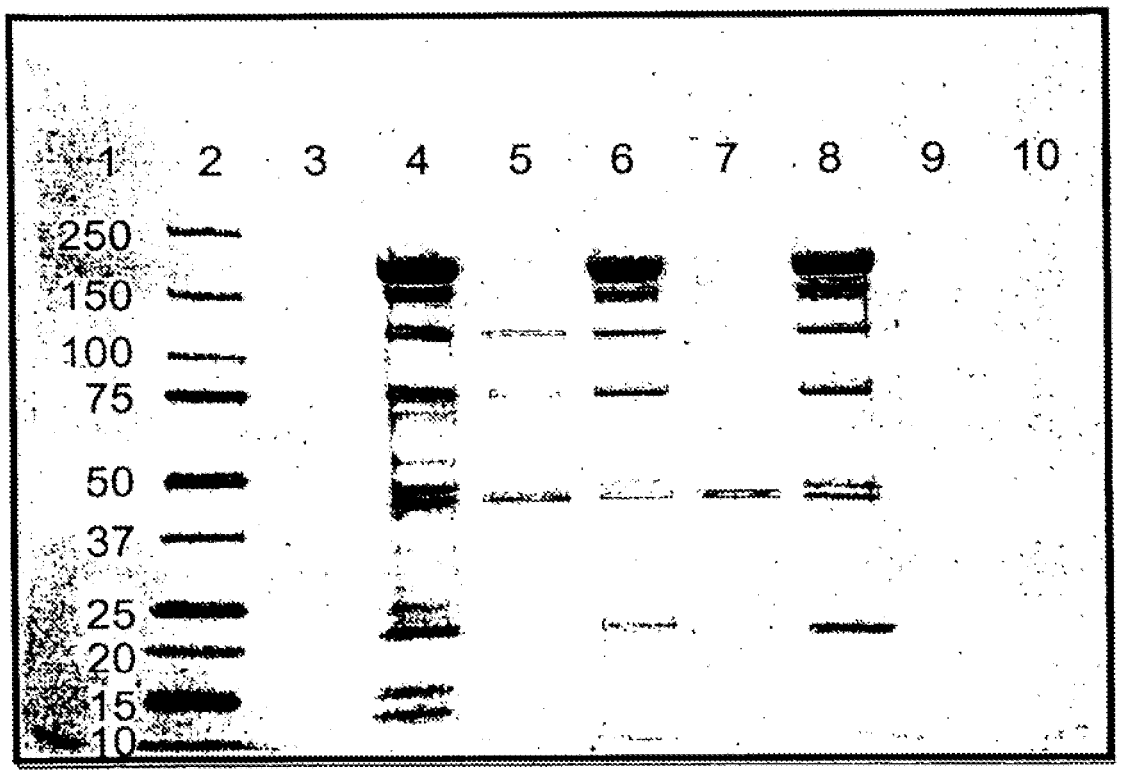
FIG. 3 shows the SDS PAGE results for Examples 28 and 29.

The SDS-PAGE gel is shown in FIG. 3. Lanes 1, 3 9 and 10 are empty. Lane 2 is a marker with 5 ml loaded, Lane 4 is the feed control with 10 ml loaded. Lane 5 is Supernatant at pH of 3.2 with 10 ml loaded. Lane 6 is Elution at pH of 3.2 with 10 ml loaded. Lane 7 is Supernatant at pH of 3.5 with 10 ml loaded. Lane 8 is Elution at pH of 3.5 with 10 ml loaded.

Under non-reducing conditions the feed (lane 4) shows intact IgG at ~200 kDa and Ig fragments bands at 150 kDa, 120 kDa, 75 kDa, and 40 kDa. The supernatants at elution pH 3.2 (lanes) and pH 3.5 (lane 7) show traces of a certain population of IgG fragments, but they contain very little intact IgG. The profile of species in the elution samples at pH 3.2 and 3.5 (lane 6 and 8) shows intact IgG along with a different fragment population.

Example 29

This Example Illustrates the Selective Binding and Subsequent Elution of Monomeric IgG Versus Aggregated IgG from an Un-clarified Cell Culture Fluid Using poly(4-vinyl pyridine) PVP Supernatant and elution samples from examples 23 and 25 were analyzed by sodium dodecyl sulfate polyacrylamide gel electrophoresis (SDS-PAGE) as described in example 28.

As depicted in the SDS-PAGE of FIG. 3 from example 28, the starting cell culture fluid (lane 4) shows a band corresponding to high molecular weight IgG (aggregates) at the top (entrance) of the gel as well as the expected bands corresponding to monomeric IgG. The supernatant and elution samples in lanes 5 & 7 and 6 & 8 are free of IgG aggregates as seen by the absence of that high molecular weight IgG band. Additionally, the bands corresponding to monomeric IgG are clearly observed in the elution samples (lanes 6 & 8.

What is claimed:

1. A method for purifying IgG antibody from an unclarified mixture containing impurities comprising:
   a. providing the mixture at a set of conditions,
   b. adding one or more polymers, soluble in said mixture under the set of conditions and capable of reversibly and selectively binding to at least the IgG antibody, said one or more polymers being one or more polyvinyl pyridine-containing polymers;
   c. mixing the one or more solubilized polymers throughout the mixture;
   d. precipitating the one or more polymers and at least the bound IgG antibody out of solution by changing the set of conditions in the mixture; and
   e. separating the precipitated polymer and at least the bound IgG antibody from the mixture.

2. The method of claim 1 wherein the one or more polymers are precipitated by a change in pH.

3. The method of claim 1 wherein the one or more polymers are solubilized and precipitated by a change in pH.

* * * * *